US006472367B1

(12) United States Patent
Blaschuk et al.

(10) Patent No.: US 6,472,367 B1
(45) Date of Patent: *Oct. 29, 2002

(54) COMPOUNDS AND METHODS FOR MODULATING OB-CADHERIN MEDIATED CELL ADHESION

(75) Inventors: Orest W. Blaschuk, Westmount; James Matthew Symonds, Ottawa; Barbara J. Gour, Kemptville, all of (CA)

(73) Assignee: Adherex Technologies, Inc., Ottawa (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

(21) Appl. No.: 09/073,040

(22) Filed: May 5, 1998

(51) Int. Cl.$^7$ ........................ A61K 38/08; A61K 38/12; A61K 38/16
(52) U.S. Cl. ............................... 514/9; 514/11; 514/12; 514/16; 514/17; 514/18; 530/317; 530/324; 530/326; 530/327; 530/328
(58) Field of Search .......................... 424/184.1, 185.1; 530/300, 317, 324, 325, 326–330; 544/2, 8; 514/9, 11, 12, 16, 17, 18

(56) References Cited

U.S. PATENT DOCUMENTS

| 5,597,725 | A | | 1/1997 | Suzuki ........................ 435/328 |
| 5,639,634 | A | | 6/1997 | Suzuki ........................ 435/69.1 |
| 5,646,250 | A | | 7/1997 | Suzuki ........................ 530/350 |
| 5,811,514 | A | * | 9/1998 | Bard et al. |
| 5,869,638 | A | * | 2/1999 | Takeshita et al. .......... 536/23.5 |
| 5,916,771 | A | * | 6/1999 | Hori et al. |
| 6,060,595 | A | * | 5/2000 | Scaglioni et al. ......... 536/23.72 |
| 6,082,713 | A | * | 7/2000 | Manly et al. .............. 435/69.1 |

FOREIGN PATENT DOCUMENTS

| GB | 2 282 379 A | 4/1995 |
| WO | WO 91/04745 | 4/1991 |
| WO | WO 96/27387 | 9/1996 |
| WO | WO 98/02452 | 1/1998 |

OTHER PUBLICATIONS

Sloostra Molecular Diversity 1: 87–96(1995).*
Kahan Curon. Opin Immunol. 4:553–560 (1992).*
Edgington Biotechnology 10:383–389 (1992).*
Ward Therapeutic Immunology 1: 165–171 (1994).*
Albeles Et Al. FASEB Journal 8: 504–512 (1994).*
Kogan Et Al. J. Biological Chem. 270: 14047–14055 (1995).*
Rozdzinski Et Al. J. Infect. Dis 168: 1422–1428 (1993).*
Ngo Et Al. In The Protein Folding and Tertiary Structure Prediction, Merz and Le Grand (Eds) Birkhauser Boston 1994.*

Bussemakers et al., "The role of OB–cadherin in human prostate cancer," *Proceedings of the American Association for Cancer Research* 39:500,#3405, Mar. 1998.
Klopfenstein et al., "Increased N–cadherin mediated adhesion does not reduce invasion of Rous sarcoma virus–transformed astrocycle–like WC5 cells," *Proceedings of the American Association for Cancer Research* 34:33, #195, Mar. 1993.
Nagashima et al., "Invasion properties in malignant gliomas—Expression of N–cadherin mRNA in gliomas," *Proceedings of the American Association for Cancer Proceedings* 37:68, #473, Mar. 1996.
Tsutsui et al., "Expression of Cadherin–Catenin Complexes in Human Leukemia Cell Lines," *Journal of Biochemistry* 120(5):1034–1039, Nov. 1996.
Getsios et al., "Regulated Expression of Cadherin–6 and Cadherin–11 in the Glandular Epithelial and Stromal Cells of the Human Endometrium," *Developmental Dynamics* 211: 238–247, 1998.
Matsuyoshi and Imamura, "Multiple Cadherins Are Expressed in Human Fibroblasts," *Biochemical And Biophysical Research Communications* 235: 355–358, 1997.
Munro and Blaschuk, In: *Cell Adhesion and Invasion in Cancer Metastasis*, P. Brodt (ed.), RG Landes Co., Austin, Texas, 1996, Chapter 3, "The Structure, Function and Regulation of Cadherins," pp. 17–34.
Okazaki et al., "Molecular Cloning and Characterization of OB–cadherin, a New Member of Cadherin Family Expressed in Osteoblasts," *The Journal of Biological Chemistry* 269(16): 12092–12098, 1994.
Shibata et al., "Simultaneous expression of cadherin–11 in signet–ring cell carcinoma and stromal cells of diffuse–type gastric cancer," *Cancer Letters* 99: 147–153, 1996.
Shimazui et al., "Complex Cadherin Expression in Renal Cell Carcinoma," *Cancer Research* 56: 3234, 3237, 1996.
Simonneau et al., "Cadherin 11 Expression Marks the Mesenchymal Phenotype: Towards New Functions for Cadherins?," *Cell Adhesion and Communication* 3: 115–130, 1995.
Suzuki et al., "Diversity of the cadherin family: evidence for eight new cadherins in nervous tissue," *Cell Regulation* 2: 261–270. 1991.

(List continued on next page.)

*Primary Examiner*—Marianne P. Allen
(74) *Attorney, Agent, or Firm*—Seed Intellectual Property Law Group pllc

(57) ABSTRACT

Modulating agents for inhibiting or enhancing OB-cadherin mediated cell adhesion are provided. The modulating agents comprise one or more of: (a) an OB-cadherin CAR sequence; (b) a peptide analogue or peptidomimetic thereof; (c) an antibody or antigen-binding fragment thereof that specifically binds an OB-cadherin CAR sequence; and/or (d) a polynucleotide encoding any of the foregoing peptide sequences. Methods for using such modulating agents for modulating OB-cadherin-mediated cell adhesion in a variety of contexts are also provided.

14 Claims, 6 Drawing Sheets

OTHER PUBLICATIONS

Lutz et al., "Antibody Recognition of Peptide Sequences from the Cell–Cell Adhesion Proteins: N– and E–cadherins," *Peptide Research* 9(5): 233–239, 1996.

Tanihara et al., "Cloning of Five Human Cadherins Clarifies Characteristic Features of Cadherin Extracellular Domain and Provides Further Evidence for Two Structurally Different Types of Cadherin," *Cell Adhesion and Communication* 2: 15–26, 1994.

* cited by examiner

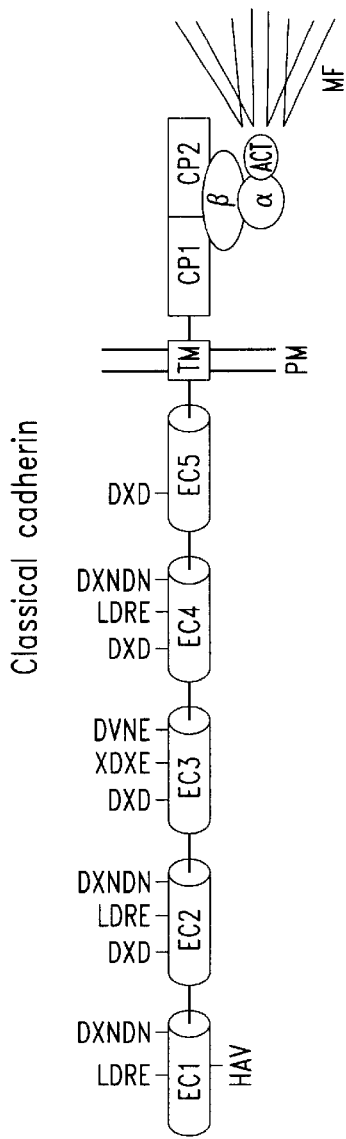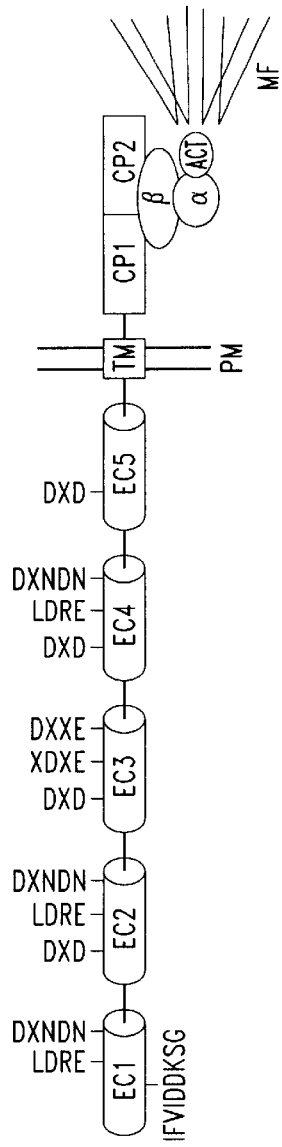

Human GWVWNQFFVIEEYTGPDPVLVGRLHSDIDSGDGNIKYILSGEGAG
Mouse GWVWNQFFVIEEYTGPDPVLVGRLHSDIDSGDGNIKYILSGEGAG Human TIFVIDDKSGNIHATKTLDREERAQYTLMAQAVDRDTNRPLEPPS
Mouse TIFVIDDKSGNIHATKTLDREERAQYTLMAQAVDRDTNRPLEPPS Human EFIVKVQDINDNPPEF
Mouse EFIVKVQDINDNPPEF

Fig. 2

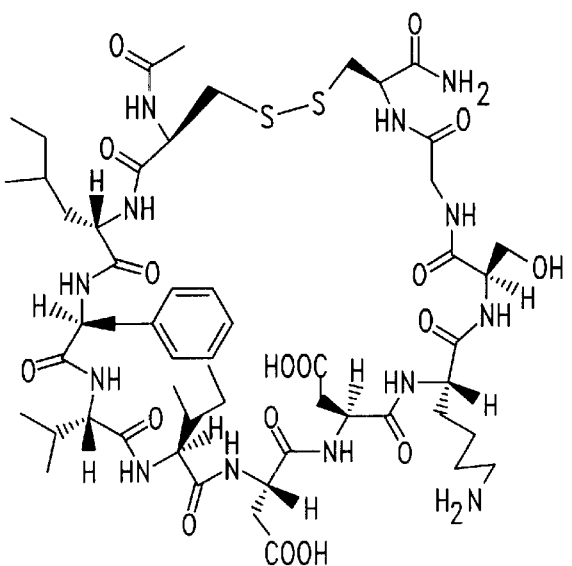
N-Ac-CIFVIDDKSGC-NH₂
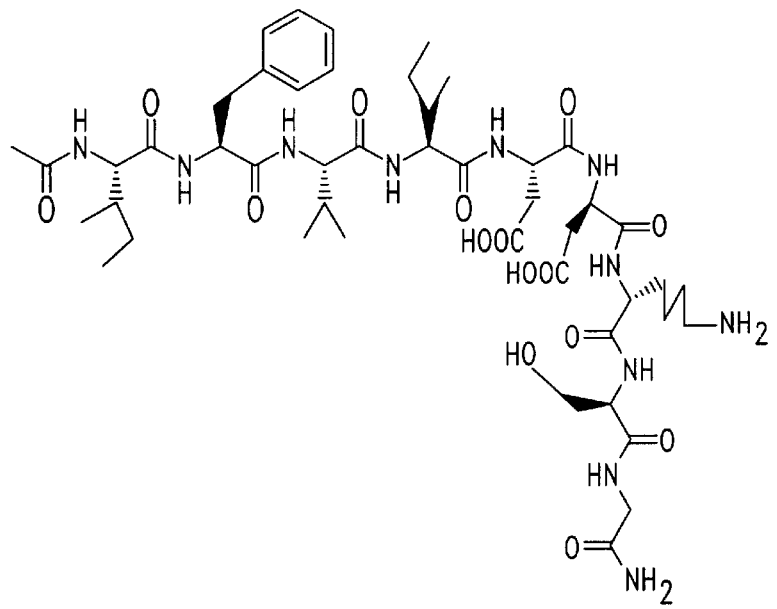
N-Ac-IFVIDDKSG-NH₂
*Fig. 3A*

SEQUENCE LISTING (1) GENERAL INFORMATION:

(iii) NUMBER OF SEQUENCES: 91

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:1:

Asp Xaa Asn Asp Asn
1               5

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:2:

Leu Asp Arg Glu
1

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:3:

Val Ile Asp Asp Lys
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:4:

Ile Asp Asp Lys Ser
1               5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:5:

Phe Val Ile Asp Asp Lys Ser Gly
1               5

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:6:

Ile Phe Val Ile Asp Asp Lys Ser Gly
1               5

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:7:

Cys Asp Asp Lys Cys
1               5

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS:
        (D) TOPOLOGY: circular (xi) SEQUENCE DESCRIPTION: SEQ ID NO:8:

Cys Val Ile Asp Asp Lys Cys
1               5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS:
        (D) TOPOLOGY: circular (xi) SEQUENCE DESCRIPTION: SEQ ID NO:9:

Cys Ile Asp Asp Lys Ser Cys
1               5

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS:
            (D) TOPOLOGY: circular (xi) SEQUENCE DESCRIPTION: SEQ ID NO:10:

Cys Phe Val Ile Asp Asp Lys Ser Gly Cys
1               5                   10

(2) INFORMATION FOR SEQ ID NO:11:

(i) SEQUENCE CHARACTERISTICS:
            (A) LENGTH: 11 amino acids
            (B) TYPE: amino acid
            (C) STRANDEDNESS:
            (D) TOPOLOGY: circular (xi) SEQUENCE DESCRIPTION: SEQ ID NO:11:

Cys Ile Phe Val Ile Asp Asp Lys Ser Gly Cys
1               5                   10

(2) INFORMATION FOR SEQ ID NO:12:

(i) SEQUENCE CHARACTERISTICS:
            (A) LENGTH: 106 amino acids
            (B) TYPE: amino acid
            (C) STRANDEDNESS:
            (D) TOPOLOGY: linear (xi) SEQUENCE DESCRIPTION: SEQ ID NO:12:

Gly Trp Val Trp Asn Gln Phe Phe Val Ile Glu Glu Tyr Thr Gly Pro
1               5                   10                  15

Asp Pro Val Leu Val Gly Arg Leu His Ser Asp Ile Asp Ser Gly Asp
                20                  25                  30

Gly Asn Ile Lys Tyr Ile Leu Ser Gly Glu Gly Ala Gly Thr Ile Phe
            35                  40                  45

Val Ile Asp Asp Lys Ser Gly Asn Ile His Ala Thr Lys Thr Leu Asp
        50                  55                  60

Arg Glu Glu Arg Ala Gln Tyr Thr Leu Met Ala Gln Ala Val Asp Arg
65                  70                  75                  80

Asp Thr Asn Arg Pro Leu Glu Pro Pro Ser Glu Phe Ile Val Lys Val
                85                  90                  95

Gln Asp Ile Asn Asp Asn Pro Pro Glu Phe
                100                 105

(2) INFORMATION FOR SEQ ID NO:13:

(i) SEQUENCE CHARACTERISTICS:
            (A) LENGTH: 106 amino acids
            (B) TYPE: amino acid
            (C) STRANDEDNESS:
            (D) TOPOLOGY: linear (xi) SEQUENCE DESCRIPTION: SEQ ID NO:13:

Gly Trp Val Trp Asn Gln Phe Phe Val Ile Glu Glu Tyr Thr Gly Pro
1               5                   10                  15

```
Asp Pro Val Leu Val Gly Arg Leu His Ser Asp Ile Asp Ser Gly Asp
            20                  25                  30
Gly Asn Ile Lys Tyr Ile Leu Ser Gly Glu Gly Ala Gly Thr Ile Phe
        35                  40                  45
Val Ile Asp Asp Lys Ser Gly Asn Ile His Ala Thr Lys Thr Leu Asp
    50                  55                  60
Arg Glu Glu Arg Ala Gln Tyr Thr Leu Met Ala Gln Ala Val Asp Arg
65                  70                  75                  80
Asp Thr Asn Arg Pro Leu Glu Pro Pro Ser Glu Phe Ile Val Lys Val
                85                  90                  95
Gln Asp Ile Asn Asp Asn Pro Pro Glu Phe
            100                 105

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:14:

Lys Asp Asp Lys Asp
1               5

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:15:

Tyr Ile Gly Ser Arg
1               5

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:16:

Cys Ile Asp Asp Lys Ser Gly Cys
1               5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:17:

Cys Ile Asp Asp Lys Cys
1               5

(2) INFORMATION FOR SEQ ID NO:18:

(i) SEQUENCE CHARACTERISTICS:
```

(A) LENGTH: 6 amino acids
        (B) TYPE: amino acid
        (C) STRANDEDNESS:
        (D) TOPOLOGY: circular (xi) SEQUENCE DESCRIPTION: SEQ ID NO:18:

Cys Asp Asp Lys Ser Cys
1               5

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS:
        (D) TOPOLOGY: circular (ix) FEATURE:
        (A) NAME/KEY: Modified-site
        (B) LOCATION: 5
        (D) OTHER INFORMATION: /note= "Where Xaa is
            beta,beta-dimethyl cysteine"

(xi) SEQUENCE DESCRIPTION: SEQ ID NO:19:

Cys Asp Asp Lys Xaa
1               5

(2) INFORMATION FOR SEQ ID NO:20:

(i) SEQUENCE CHARACTERISTICS:
        (A) LENGTH: 10 amino acids
        (B) TYPE: amino acid
        (C) STRANDEDNESS:
        (D) TOPOLOGY: both (ix) FEATURE:
        (A) NAME/KEY: Modified-site
        (B) LOCATION: 2
        (D) OTHER INFORMATION: /note= "Where Xaa is
            beta,beta-tetramethylene cysteine"

(xi) SEQUENCE DESCRIPTION: SEQ ID NO:20:

Ile Xaa Val Ile Asp Asp Lys Ser Cys Glu
1               5                   10

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS:
        (D) TOPOLOGY: both (ix) FEATURE:
        (A) NAME/KEY: Modified-site
        (B) LOCATION: 2
        (D) OTHER INFORMATION: /note= "Where Xaa is
            beta,beta=pentamethylene cysteine"

(xi) SEQUENCE DESCRIPTION: SEQ ID NO:21:

Ile Xaa Val Ile Asp Asp Lys Ser Gly Cys
1               5                   10

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS:
        (D) TOPOLOGY: circular

```
    (ix) FEATURE:
         (A) NAME/KEY: Modified-site
         (B) LOCATION: 1
         (D) OTHER INFORMATION: /note= "Where Xaa is
             beta-mercptopropionic acid"

(xi) SEQUENCE DESCRIPTION: SEQ ID NO:22:

Xaa Val Ile Asp Asp Lys Ser Gly Cys
1               5

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS:
        (D) TOPOLOGY: circular (ix) FEATURE:
         (A) NAME/KEY: Modified-site
         (B) LOCATION: 1
         (D) OTHER INFORMATION: /note= "Where Xaa is
             beta,beta-pentamethylene-beta-mercaptopropionic acid"

(xi) SEQUENCE DESCRIPTION: SEQ ID NO:23:

Xaa Val Ile Asp Asp Lys Ser Gly Cys
1               5

(2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:24:

Ile Asp Asp Lys Ser Gly
1               5

(2) INFORMATION FOR SEQ ID NO:25:

(i) SEQUENCE CHARACTERISTICS:
        (A) LENGTH: 5 amino acids
        (B) TYPE: amino acid
        (C) STRANDEDNESS:
        (D) TOPOLOGY: linear (ix) FEATURE:
         (A) NAME/KEY: Modified-site
         (B) LOCATION: 4
         (D) OTHER INFORMATION: /note= "Where Xaa is D-Serine"

(xi) SEQUENCE DESCRIPTION: SEQ ID NO:25:

Asp Asp Lys Xaa Ser
1               5

(2) INFORMATION FOR SEQ ID NO:26:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:26:

Lys Ile Asp Asp Lys Ser Gly Asp
1               5
```

(2) INFORMATION FOR SEQ ID NO:27:

(i) SEQUENCE CHARACTERISTICS:
        (A) LENGTH: 4 amino acids
        (B) TYPE: amino acid
        (C) STRANDEDNESS:
        (D) TOPOLOGY: circular (xi) SEQUENCE DESCRIPTION: SEQ ID NO:27:

Trp Gly Gly Trp
1

(2) INFORMATION FOR SEQ ID NO:28:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:28:

Leu Tyr His Tyr
1

(2) INFORMATION FOR SEQ ID NO:29:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:29:

Ser His Ala Val Ser Ser
1               5

(2) INFORMATION FOR SEQ ID NO:30:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:30:

Ala His Ala Val Asp Ile
1               5

(2) INFORMATION FOR SEQ ID NO:31:

(i) SEQUENCE CHARACTERISTICS:
        (A) LENGTH: 9 amino acids
        (B) TYPE: amino acid
        (C) STRANDEDNESS:
        (D) TOPOLOGY: circular (xi) SEQUENCE DESCRIPTION: SEQ ID NO:31:

Cys Val Ile Asp Asp Lys Ser Gly Cys
1               5

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:32:

```
Ile Asp Asp Lys
  1
```

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:33:

```
Asp Asp Lys Ser
  1
```

(2) INFORMATION FOR SEQ ID NO:34:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:34:

```
Val Ile Asp Asp Lys Ser
  1               5
```

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:35:

```
Asp Asp Lys Ser Gly
  1               5
```

(2) INFORMATION FOR SEQ ID NO:36:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:36:

```
Val Ile Asp Asp Lys Ser Gly
  1               5
```

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:37:

```
Phe Val Ile Asp Asp Lys
  1               5
```

(2) INFORMATION FOR SEQ ID NO:38:

(i) SEQUENCE CHARACTERISTICS:
        (A) LENGTH: 7 amino acids

```
        (B) TYPE: amino acid
        (C) STRANDEDNESS:
        (D) TOPOLOGY: linear (xi) SEQUENCE DESCRIPTION: SEQ ID NO:38:

Phe Val Ile Asp Asp Lys Ser
1               5

(2) INFORMATION FOR SEQ ID NO:39:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:39:

Ile Phe Val Ile Asp Asp Lys
1               5

(2) INFORMATION FOR SEQ ID NO:40:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:40:

Ile Phe Val Ile Asp Asp Lys Ser
1               5

(2) INFORMATION FOR SEQ ID NO:41:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:41:

Cys Ile Asp Asp Lys Cys
1               5

(2) INFORMATION FOR SEQ ID NO:42:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:42:

Cys Asp Asp Lys Ser Cys
1               5

(2) INFORMATION FOR SEQ ID NO:43:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:43:

Cys Val Ile Asp Asp Lys Ser Cys
1               5
```

(2) INFORMATION FOR SEQ ID NO:44:

(i) SEQUENCE CHARACTERISTICS:
        (A) LENGTH: 7 amino acids
        (B) TYPE: amino acid
        (C) STRANDEDNESS:
        (D) TOPOLOGY: circular (xi) SEQUENCE DESCRIPTION: SEQ ID NO:44:

Cys Asp Asp Lys Ser Gly Cys
1               5

(2) INFORMATION FOR SEQ ID NO:45:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:45:

Cys Ile Asp Asp Lys Ser Gly Cys
1               5

(2) INFORMATION FOR SEQ ID NO:46:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:46:

Cys Phe Val Ile Asp Asp Lys Cys
1               5

(2) INFORMATION FOR SEQ ID NO:47:

(i) SEQUENCE CHARACTERISTICS:
        (A) LENGTH: 9 amino acids
        (B) TYPE: amino acid
        (C) STRANDEDNESS:
        (D) TOPOLOGY: circular (xi) SEQUENCE DESCRIPTION: SEQ ID NO:47:

Cys Phe Val Ile Asp Asp Lys Ser Cys
1               5

(2) INFORMATION FOR SEQ ID NO:48:

(i) SEQUENCE CHARACTERISTICS:
        (A) LENGTH: 9 amino acids
        (B) TYPE: amino acid
        (C) STRANDEDNESS:
        (D) TOPOLOGY: circular (xi) SEQUENCE DESCRIPTION: SEQ ID NO:48:

Cys Ile Phe Val Ile Asp Asp Lys Cys
1               5

(2) INFORMATION FOR SEQ ID NO:49:

(i) SEQUENCE CHARACTERISTICS:
        (A) LENGTH: 10 amino acids
        (B) TYPE: amino acid
        (C) STRANDEDNESS:
        (D) TOPOLOGY: circular (xi) SEQUENCE DESCRIPTION: SEQ ID NO:49:

Cys Ile Phe Val Ile Asp Asp Lys Ser Cys
1               5                   10

(2) INFORMATION FOR SEQ ID NO:50:

(i) SEQUENCE CHARACTERISTICS:
        (A) LENGTH: 4 amino acids
        (B) TYPE: amino acid
        (C) STRANDEDNESS:
        (D) TOPOLOGY: circular (xi) SEQUENCE DESCRIPTION: SEQ ID NO:50:

Asp Asp Asp Lys
1

(2) INFORMATION FOR SEQ ID NO:51:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:51:

Asp Ile Asp Asp Lys
1               5

(2) INFORMATION FOR SEQ ID NO:52:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:52:

Asp Val Ile Asp Asp Lys
1               5

(2) INFORMATION FOR SEQ ID NO:53:

(i) SEQUENCE CHARACTERISTICS:
        (A) LENGTH: 7 amino acids
        (B) TYPE: amino acid
        (C) STRANDEDNESS:
        (D) TOPOLOGY: circular (xi) SEQUENCE DESCRIPTION: SEQ ID NO:53:

Asp Phe Val Ile Asp Asp Lys
1               5

(2) INFORMATION FOR SEQ ID NO:54:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:54:

Asp Ile Phe Val Ile Asp Asp Lys
1               5

(2) INFORMATION FOR SEQ ID NO:55:

(i) SEQUENCE CHARACTERISTICS:

(A) LENGTH: 4 amino acids
        (B) TYPE: amino acid
        (C) STRANDEDNESS:
        (D) TOPOLOGY: circular (xi) SEQUENCE DESCRIPTION: SEQ ID NO:55:

Glu Asp Asp Lys
1

(2) INFORMATION FOR SEQ ID NO:56:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:56:

Glu Ile Asp Asp Lys
1               5

(2) INFORMATION FOR SEQ ID NO:57:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:57:

Glu Val Ile Asp Asp Lys
1               5

(2) INFORMATION FOR SEQ ID NO:58:

(i) SEQUENCE CHARACTERISTICS:
        (A) LENGTH: 7 amino acids
        (B) TYPE: amino acid
        (C) STRANDEDNESS:
        (D) TOPOLOGY: circular (xi) SEQUENCE DESCRIPTION: SEQ ID NO:58:

Glu Phe Val Ile Asp Asp Lys
1               5

(2) INFORMATION FOR SEQ ID NO:59:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:59:

Glu Ile Phe Val Ile Asp Asp Lys
1               5

(2) INFORMATION FOR SEQ ID NO:60:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:60:

Lys Ile Asp Asp Lys Asp
1               5

(2) INFORMATION FOR SEQ ID NO:61:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:61:

Lys Asp Asp Lys Ser Asp
1               5

(2) INFORMATION FOR SEQ ID NO:62:

(i) SEQUENCE CHARACTERISTICS:
        (A) LENGTH: 7 amino acids
        (B) TYPE: amino acid
        (C) STRANDEDNESS:
        (D) TOPOLOGY: circular (xi) SEQUENCE DESCRIPTION: SEQ ID NO:62:

Lys Val Ile Asp Asp Lys Asp
1               5

(2) INFORMATION FOR SEQ ID NO:63:

(i) SEQUENCE CHARACTERISTICS:
        (A) LENGTH: 7 amino acids
        (B) TYPE: amino acid
        (C) STRANDEDNESS:
        (D) TOPOLOGY: circular (xi) SEQUENCE DESCRIPTION: SEQ ID NO:63:

Lys Ile Asp Asp Lys Ser Asp
1               5

(2) INFORMATION FOR SEQ ID NO:64:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:64:

Lys Val Ile Asp Asp Lys Ser Asp
1               5

(2) INFORMATION FOR SEQ ID NO:65:

(i) SEQUENCE CHARACTERISTICS:
        (A) LENGTH: 7 amino acids
        (B) TYPE: amino acid
        (C) STRANDEDNESS:
        (D) TOPOLOGY: circular (xi) SEQUENCE DESCRIPTION: SEQ ID NO:65:

Lys Asp Asp Lys Ser Gly Asp
1               5

(2) INFORMATION FOR SEQ ID NO:66:

(i) SEQUENCE CHARACTERISTICS:
        (A) LENGTH: 9 amino acids
        (B) TYPE: amino acid
        (C) STRANDEDNESS:
        (D) TOPOLOGY: circular (xi) SEQUENCE DESCRIPTION: SEQ ID NO:66:

Lys Val Ile Asp Asp Lys Ser Gly Asp
1               5

(2) INFORMATION FOR SEQ ID NO:67:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:67:

Lys Phe Val Ile Asp Asp Lys Asp
1               5

(2) INFORMATION FOR SEQ ID NO:68:

(i) SEQUENCE CHARACTERISTICS:
        (A) LENGTH: 9 amino acids
        (B) TYPE: amino acid
        (C) STRANDEDNESS:
        (D) TOPOLOGY: circular (xi) SEQUENCE DESCRIPTION: SEQ ID NO:68:

Lys Phe Val Ile Asp Asp Lys Ser Asp
1               5

(2) INFORMATION FOR SEQ ID NO:69:

(i) SEQUENCE CHARACTERISTICS:
        (A) LENGTH: 10 amino acids
        (B) TYPE: amino acid
        (C) STRANDEDNESS:
        (D) TOPOLOGY: circular (xi) SEQUENCE DESCRIPTION: SEQ ID NO:69:

Lys Phe Val Ile Asp Asp Lys Ser Gly Asp
1               5                   10

(2) INFORMATION FOR SEQ ID NO:70:

(i) SEQUENCE CHARACTERISTICS:
        (A) LENGTH: 9 amino acids
        (B) TYPE: amino acid
        (C) STRANDEDNESS:
        (D) TOPOLOGY: circular (xi) SEQUENCE DESCRIPTION: SEQ ID NO:70:

Lys Ile Phe Val Ile Asp Asp Lys Asp
1               5

(2) INFORMATION FOR SEQ ID NO:71:

(i) SEQUENCE CHARACTERISTICS:
        (A) LENGTH: 10 amino acids
        (B) TYPE: amino acid
        (C) STRANDEDNESS:
        (D) TOPOLOGY: circular (xi) SEQUENCE DESCRIPTION: SEQ ID NO:71:

Lys Ile Phe Val Ile Asp Asp Lys Ser Asp
1               5                   10

(2) INFORMATION FOR SEQ ID NO:72:

```
    (i) SEQUENCE CHARACTERISTICS:
        (A) LENGTH: 11 amino acids
        (B) TYPE: amino acid
        (C) STRANDEDNESS:
        (D) TOPOLOGY: circular (xi) SEQUENCE DESCRIPTION: SEQ ID NO:72:

Lys Ile Phe Val Ile Asp Asp Lys Ser Gly Asp
1               5                   10

(2) INFORMATION FOR SEQ ID NO:73:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:73:

Val Ile Asp Asp Lys
1               5

(2) INFORMATION FOR SEQ ID NO:74:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:74:

Ile Asp Asp Lys Ser
1               5

(2) INFORMATION FOR SEQ ID NO:75:

(i) SEQUENCE CHARACTERISTICS:
        (A) LENGTH: 6 amino acids
        (B) TYPE: amino acid
        (C) STRANDEDNESS:
        (D) TOPOLOGY: circular (xi) SEQUENCE DESCRIPTION: SEQ ID NO:75:

Val Ile Asp Asp Lys Ser
1               5

(2) INFORMATION FOR SEQ ID NO:76:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:76:

Asp Asp Lys Ser Gly
1               5

(2) INFORMATION FOR SEQ ID NO:77:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:77:

Lys Asp Asp Lys Glu
```

```
1               5

(2) INFORMATION FOR SEQ ID NO:78:

(i) SEQUENCE CHARACTERISTICS:
          (A) LENGTH: 6 amino acids
          (B) TYPE: amino acid
          (C) STRANDEDNESS:
          (D) TOPOLOGY: circular (xi) SEQUENCE DESCRIPTION: SEQ ID NO:78:

Lys Ile Asp Asp Lys Glu
1               5

(2) INFORMATION FOR SEQ ID NO:79:

(i) SEQUENCE CHARACTERISTICS:
          (A) LENGTH: 6 amino acids
          (B) TYPE: amino acid
          (C) STRANDEDNESS:
          (D) TOPOLOGY: circular (xi) SEQUENCE DESCRIPTION: SEQ ID NO:79:

Lys Asp Asp Lys Ser Glu
1               5

(2) INFORMATION FOR SEQ ID NO:80:

(i) SEQUENCE CHARACTERISTICS:
          (A) LENGTH: 7 amino acids
          (B) TYPE: amino acid
          (C) STRANDEDNESS:
          (D) TOPOLOGY: circular (xi) SEQUENCE DESCRIPTION: SEQ ID NO:80:

Lys Val Ile Asp Asp Lys Glu
1               5

(2) INFORMATION FOR SEQ ID NO:81:

(i) SEQUENCE CHARACTERISTICS:
          (A) LENGTH: 7 amino acids
          (B) TYPE: amino acid
          (C) STRANDEDNESS:
          (D) TOPOLOGY: circular (xi) SEQUENCE DESCRIPTION: SEQ ID NO:81:

Lys Ile Asp Asp Lys Ser Glu
1               5

(2) INFORMATION FOR SEQ ID NO:82:

(i) SEQUENCE CHARACTERISTICS:
          (A) LENGTH: 8 amino acids
          (B) TYPE: amino acid
          (C) STRANDEDNESS:
          (D) TOPOLOGY: circular (xi) SEQUENCE DESCRIPTION: SEQ ID NO:82:

Lys Val Ile Asp Asp Lys Ser Glu
1               5

(2) INFORMATION FOR SEQ ID NO:83:

(i) SEQUENCE CHARACTERISTICS:
          (A) LENGTH: 7 amino acids
          (B) TYPE: amino acid
          (C) STRANDEDNESS:
```

(D) TOPOLOGY: circular (xi) SEQUENCE DESCRIPTION: SEQ ID NO:83:

Lys Asp Asp Lys Ser Gly Glu
1               5

(2) INFORMATION FOR SEQ ID NO:84:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:84:

Lys Ile Asp Asp Lys Ser Gly Glu
1               5

(2) INFORMATION FOR SEQ ID NO:85:

(i) SEQUENCE CHARACTERISTICS:
        (A) LENGTH: 9 amino acids
        (B) TYPE: amino acid
        (C) STRANDEDNESS:
        (D) TOPOLOGY: circular (xi) SEQUENCE DESCRIPTION: SEQ ID NO:85:

Lys Val Ile Asp Asp Lys Ser Gly Glu
1               5

(2) INFORMATION FOR SEQ ID NO:86:

(i) SEQUENCE CHARACTERISTICS:
        (A) LENGTH: 8 amino acids
        (B) TYPE: amino acid
        (C) STRANDEDNESS:
        (D) TOPOLOGY: circular (xi) SEQUENCE DESCRIPTION: SEQ ID NO:86:

Lys Phe Val Ile Asp Asp Lys Glu
1               5

(2) INFORMATION FOR SEQ ID NO:87:

(i) SEQUENCE CHARACTERISTICS:
        (A) LENGTH: 9 amino acids
        (B) TYPE: amino acid
        (C) STRANDEDNESS:
        (D) TOPOLOGY: circular (xi) SEQUENCE DESCRIPTION: SEQ ID NO:87:

Lys Phe Val Ile Asp Asp Lys Ser Glu
1               5

(2) INFORMATION FOR SEQ ID NO:88:

(i) SEQUENCE CHARACTERISTICS:
        (A) LENGTH: 10 amino acids
        (B) TYPE: amino acid
        (C) STRANDEDNESS:
        (D) TOPOLOGY: circular (xi) SEQUENCE DESCRIPTION: SEQ ID NO:88:

Lys Phe Val Ile Asp Asp Lys Ser Gly Glu
1               5                   10

(2) INFORMATION FOR SEQ ID NO:89:

```
        (i) SEQUENCE CHARACTERISTICS:
            (A) LENGTH: 9 amino acids
            (B) TYPE: amino acid
            (C) STRANDEDNESS:
            (D) TOPOLOGY: circular (xi) SEQUENCE DESCRIPTION: SEQ ID NO:89:

Lys Ile Phe Val Ile Asp Asp Lys Glu
1               5

(2) INFORMATION FOR SEQ ID NO:90:

(i) SEQUENCE CHARACTERISTICS:
            (A) LENGTH: 10 amino acids
            (B) TYPE: amino acid
            (C) STRANDEDNESS:
            (D) TOPOLOGY: circular (xi) SEQUENCE DESCRIPTION: SEQ ID NO:90:

Lys Ile Phe Val Ile Asp Asp Lys Ser Glu
1               5                   10

(2) INFORMATION FOR SEQ ID NO:91:

(i) SEQUENCE CHARACTERISTICS:
            (A) LENGTH: 11 amino acids
            (B) TYPE: amino acid
            (C) STRANDEDNESS:
            (D) TOPOLOGY: circular (xi) SEQUENCE DESCRIPTION: SEQ ID NO:91:

Lys Ile Phe Val Ile Asp Asp Lys Ser Gly Glu
1               5                   10
```

COMPOUNDS AND METHODS FOR MODULATING OB-CADHERIN MEDIATED CELL ADHESION

TECHNICAL FIELD

The present invention relates generally to methods for modulating OB-cadherin-mediated processes, and more particularly to the use of modulating agents comprising OB-cadherin cell adhesion recognition sequences, or antibodies that specifically recognize such sequences, for inhibiting or enhancing functions such as cell adhesion, tumor cell invasion and metastasis.

BACKGROUND OF THE INVENTION

Cadherins are a rapidly expanding family of calcium-dependent cell adhesion molecules (CAMs) (for review, see Munro et al., *In: Cell Adhesion and Invasion in Cancer Metastasis*, P. Brodt, ed., pp. 17–34, RG Landes Co., Austin, Tex., 1996). There are many different types of cadherins (abbreviated CADs). The most extensively studied group of CADs is known as the classical, or type I, CADs. These CADs are integral membrane glycoproteins that generally promote cell adhesion through homophilic interactions (a CAD on the surface of one cell binds to an identical CAD on the surface of another cell), although CADs also appear to be capable of forming heterotypic complexes with one another under certain circumstances and with lower affinity. Cadherins have been shown to regulate epithelial, endothelial, neural and cancer cell adhesion, with different CADs expressed on different cell types. N (neural)—cadherin is predominantly expressed by neural cells, endothelial cells and a variety of cancer cell types. E (epithelial)—cadherin is predominantly expressed by epithelial cells. Other CADs are P (placental)—cadherin, which is found in human skin and R (retinal)—cadherin. A detailed discussion of the classical cadherins is provided in Munro S B et al., *In: Cell Adhesion and Invasion in Cancer Metastasis*, P. Brodt, ed., pp. 17–34 (RG Landes Company, Austin, Tex., 1996).

The structures of the CADs are generally similar. As illustrated in FIG. 1A, CADs are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:1), DXD and LDRE (SEQ ID NO:2) are interspersed throughout the extracellular domains. The first extracellular domain (EC1) contains the classical cadherin cell adhesion recognition (CAR) sequence, HAV (His-Ala-Val), along with flanking sequences on either side of the CAR sequence that may play a role in conferring specificity. Synthetic peptides containing the CAR sequence and antibodies directed against the CAR sequence have been shown to inhibit CAD-dependent processes (Munro et al., supra; Blaschuk et al., *J. Mol. Biol.* 211:679–82, 1990; Blaschuk et al., *Develop. Biol.* 139:227–29, 1990; Alexander et al., *J. Cell. Physiol.* 156:610–18, 1993).

A second group of CADs is known as the atypical, or type II CADs (Munro et al., supra). Although the structure of these CADs is similar to that of the type I CADs, they do not contain the CAR sequence, HAV (FIG. 1B). Furthermore, the functions of the type II CADs are poorly understood.

OB-cadherin, which is also known as cadherin-11, is an atypical CAD (Okazaki et al., *J. Biol. Chem.* 269:12092–98, 1994; Suzuki et al., *Cell Regulation* 2:261–70, 1991; Munro et al., supra). This CAD can promote cell adhesion through homophilic interactions. Recent studies have shown that OB-cadherin is not expressed by well-differentiated, poorly invasive cancer cells, whereas it is expressed by invasive cancer cells (Stephen W. Byers, Georgetown University, Washington DC, personal communication; Shimazui et al., *Cancer Res.* 56:3234–37, 1996; Shibata et al., *Cancer Letters* 99:147–53, 1996). OB-cadherin levels are also high in stromal cells and osteoblasts (Shibata et al., *Cancer Letters* 99:147–53, 1996; Simonneau et al., *Cell Adhes. Commun.* 3:115–30, 1995; Matsuyoshi and Imamura, *Biochem. Biophys. Res. Commun.* 23:355–58, 1997; Okazaki et al., *J. Biol. Chem.* 269:12092–98, 1994). Collectively, these observations have led to the hypothesis that OB-cadherin may mediate the interaction between malignant tumor cells and other cell types, such as stromal cells and osteoblasts, thus facilitating tumor cell invasion and metastasis.

OB-cadherin is expressed in certain specific cell types. In some invasive cancer cells, OB-cadherin is not only found at sites of cell—cell contact, but it is also found in lamellopodia-like projections which do not interact with other cells (Stephen W. Byers, Georgetown University, Washington DC, personal communication). These observations suggest that OB-cadherin may also play a role in modulating cell-substrate interactions. In adipocytes, OB-cadherin is the only known expressed cadherin. OB-cadherin is therefore likely to mediate adhesion between adipocytes, and it is likely to be an important regulator of adipogenesis. Another cell type that expresses OB-cadherin is the pericyte (also known as the peri-endothelial cell). Pericytes are contractile cells which are similar to smooth muscle cells. They encircle the endothelial cells of blood vessels. Pericytes are involved in maintaining the structural integrity of blood vessels (Hanahan, *Science* 277:48–50, 1997; Lindahl et al., *Science* 277:242–245, 1997). Loss of pericytes causes blood vessels to regress.

Notwithstanding these recent advances, OB-cadherin function remains poorly understood at the biological and molecular levels. Accordingly, there is a need in the art for identifying sequences involved in modulating OB-cadherin-dependent cell adhesion, and for the development of methods employing such sequences to inhibit cancer cell adhesion, invasion and metastasis. The present invention fulfills these needs and further provides other related advantages.

SUMMARY OF THE INVENTION

Briefly stated, this invention provides compositions and methods for modulating OB-cadherin-mediated processes, such as cancer cell adhesion, invasion, and metastasis. Within certain aspects, cell adhesion modulating agents capable of modulating OB-cadherin mediated cell adhesion are provided. Such modulating agents may comprise at least one of: (a) a native OB-cadherin CAR sequence; (b) an analogue of a native OB-cadherin CAR sequence that is capable of modulating OB-cadherin-mediated cell adhesion; (c) a non-peptide peptidomimetic of an OB-cadherin CAR sequence that is capable of modulating OB-cadherin-mediated cell adhesion; (d) an antibody, or antigen-binding fragment thereof, that specifically binds an OB-cadherin CAR sequence; and/or (e) a polynucleotide encoding a native OB-cadherin CAR sequence or analogue thereof that is capable of modulating OB-cadherin-mediated cell adhesion. Certain preferred modulating agents may comprise a peptide that comprises one or more of the following peptide sequences: DDK, IDDK (SEQ ID NO:32), DDKS (SEQ ID NO:33), VIDDK (SEQ ID NO:3), IDDKS (SEQ ID NO:4), VIDDKS (SEQ ID NO:34), DDKSG (SEQ ID NO:35), IDDKSG (SEQ ID NO:24), VIDDKSG (SEQ ID NO:36), FVIDDK (SEQ ID NO:37), FVIDDKS (SEQ ID NO:38), FVIDDKSG (SEQ ID NO:5), IFVIDDK (SEQ ID NO:39), IFVIDDKS (SEQ ID NO:40) or IFVIDDKSG (SEQ ID NO:6), or an analogue or peptidomimetic of any of the foregoing peptide sequences. Within other embodiments, a modulating agent may comprise a cyclic peptide having one of the following sequences: CDDKC (SEQ ID NO:7), CIDDKC (SEQ ID NO:41), CDDKSC (SEQ ID NO:42), CVIDDKC (SEQ ID NO:8), CIDDKSC (SEQ ID NO:9), CVIDDKSC (SEQ ID NO:43), CDDKSGC (SEQ ID NO:44), CIDDKSGC (SEQ ID NO:45), CVIDDKSGC (SEQ ID NO:31), CFVIDDKC(SEQ ID NO:46), CFVIDDKSC (SEQ ID NO:47), CFVIDDKSGC (SEQ ID NO:10), CIFVIDDKC (SEQ ID NO:48), CIFVIDDKSC (SEQ ID NO:49), or CIFVIDDKSGC (SEQ ID NO:11), DDDK(SEQ ID NO:50), DIDDK (SEQ ID NO:51), DVIDDK (SEQ ID NO:52), DFVIDDK (SEQ ID NO:53), DIFVIDDK (SEQ ID NO:54), EDDK(SEQ ID NO:55), EIDDK (SEQ ID NO:56), EVIDDK (SEQ ID NO:57), EFVIDDK (SEQ ID NO:58), EIFVIDDK (SEQ ID NO:59), KDDKD (SEQ ID NO:14), KIDDKD (SEQ ID NO:60), KDDKSD (SEQ ID NO:61), KVIDDKD(SEQ ID NO:62), KIDDKSD (SEQ ID NO:63), KVIDDKSD (SEQ ID NO:64), KDDKSGD (SEQ ID NO:65), KIDDKSGD (SEQ ID NO:26), KVIDDKSGD (SEQ ID NO:66), KFVIDDKD (SEQ ID NO:67), KFVIDDKSD (SEQ ID NO:68), KFVIDDKSGD (SEQ ID NO:69), KIFVIDDKD (SEQ ID NO:70), KIFVIDDKSD (SEQ ID NO:71), KIFVIDDKSGD (SEQ ID NO:72), VIDDK (SEQ ID NO:73), IDDKS (SEQ ID NO:74), VIDDKS (SEQ ID NO:75), DDKSG (SEQ ID NO:76), IDDKSG (SEQ ID NO:24) KDDKE (SEQ ID NO:77), KIDDKE (SEQ ID NO:78), KDDKSE (SEQ ID NO:79), KVIDDKE (SEQ ID NO:80), KIDDKSE (SEQ ID NO:81), KVIDDKSE (SEQ ID NO:82), KDDKSGE (SEQ ID NO:83), KIDDKSGE (SEQ ID NO:84), KVIDDKSGE (SEQ ID NO:85), KFVIDDKE (SEQ ID NO:86), KFVIDDKSE (SEQ ID NO:87), KFVIDDKSGE (SEQ ID NO:88), KIFVIDDKE (SEQ ID NO:89), KIFVIDDKSE (SEQ ID NO:90), or KIFVIDDKSGE (SEQ ID NO:91). In certain embodiments, a modulating agent may be linked to a drug, a detectable marker, a targeting agent and/or a support material. Modulating agents may also, or alternatively, comprise one or more of: (a) a cell adhesion recognition sequence other than an OB-cadherin CAR sequence; and/or (b) an antibody or antigen-binding fragment thereof that specifically binds to a CAR sequence other than an OB-cadherin CAR sequence.

Within further aspects, pharmaceutical compositions are provided, comprising a cell adhesion modulating agent according to claim 1, in combination with a pharmaceutically acceptable carrier. Such compositions may additionally comprise a drug and/or one or more of: (a) a peptide comprising a cell adhesion recognition sequence other than an OB-cadherin CAR sequence; and/or (b) an antibody or antigen-binding fragment thereof that specifically binds to a CAR sequence other than an OB-cadherin CAR sequence.

The present invention further provides, within other aspects, methods for modulating cell adhesion, comprising contacting an OB-cadherin-expressing cell with a cell adhesion modulating agent or a pharmaceutical composition as described above. Such modulating agents and compositions may inhibit or enhance cell adhesion.

Within other aspects, the present invention provides methods for inhibiting adhesion of OB-cadherin expressing cells in a mammal, comprising administering to a mammal a cell adhesion modulating agent as described above, wherein the modulating agent inhibits OB-cadherin-mediated cell adhesion.

The present invention further provides methods for enhancing the delivery of a drug to a tumor in a mammal, comprising administering to a mammal: (a) a modulating agent as described above, wherein the modulating agent inhibits OB-cadherin-mediated cell adhesion; and (b) a drug. The modulating agent may be administered to the tumor or systemically, and may be linked to the drug and/or a targeting agent.

Within other aspects, the present invention provides methods for treating a cancer and/or inhibiting metastasis of a cancer in a mammal, comprising administering to a mammal a modulating agent as described above, wherein the modulating agent inhibits OB-cadherin-mediated cell adhesion.

The present invention further provides, within other aspects, methods for stimulating blood vessel regression in a mammal, comprising administering to a mammal a modulating agent as described above, wherein the modulating agent inhibits OB-cadherin-mediated cell adhesion.

In still further aspects, methods are provided for enhancing wound healing in a mammal, comprising administering to a mammal a modulating agent as described above, wherein the modulating agent enhances OB-cadherin-mediated cell adhesion. Such modulating agents may be linked to a support material.

Within other aspects, the present invention provides methods for enhancing adhesion of foreign tissue implanted within a mammal, comprising contacting a site of implantation of foreign tissue in a mammal with a modulating agent as described above, wherein the modulating agent enhances OB-cadherin-mediated cell adhesion. Such foreign tissue includes skin grafts and organ implants.

In further aspects, methods are provided for increasing vasopermeability in a mammal, comprising administering to a mammal a modulating agent as described above, wherein the modulating agent inhibits OB-cadherin mediated cell adhesion.

Within other aspects, the present invention provides methods for enhancing drug delivery to the central nervous system of a mammal, comprising administering to a mammal a drug and a modulating agent as described above, wherein the modulating agent inhibits OB-cadherin mediated cell adhesion.

Within further aspects, methods are provided for detecting the presence of OB-cadherin-expressing cells in a sample, comprising: (a) contacting a sample with an antibody or an antigen-binding fragment thereof that binds to an OB-cadherin CAR sequence under conditions and for a time sufficient to allow formation of an antibody-cadherin complex; and (b) detecting the level of antibody-cadherin complex, and therefrom detecting the presence of cadherin expressing cells in a sample.

The present invention further provides kits for detecting the presence of OB-cadherin-expressing cells in a sample, comprising: (a) an antibody or antigen-binding fragment thereof that binds to an OB-cadherin CAR sequence; and (b) a detection reagent.

Within further aspects, the present invention provides methods for identifying a compound capable of modulating OB-cadherin-mediated cell adhesion, comprising: (a) contacting an antibody or antigen-binding fragment that specifically binds to an OB-cadherin CAR sequence with a test compound; and (b) detecting the level of antibody or fragment that binds to the test compound, and therefrom identifying a compound capable of modulating cadherin-mediated cell adhesion.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1A is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:1), DXD and LDRE (SEQ ID NO:2). The CAR sequence, HAV, is shown within EC1. Cytoplasmic proteins β-catenin (β), α-catenin (α) and α-actinin (ACT), which mediate the interaction between CADs and microfilaments (MF) are also shown. FIG. 1B is a diagram depicting the structure of the atypical CAD known as OB-cadherin. The CAR sequence, IFVIDDKSG (SEQ ID NO:6), is shown within EC1.

FIG. 2 provides the amino acid sequences of representative mammalian OB-cadherin EC1 domains: human OB-cadherin (SEQ ID NO:12) and mouse OB-cadherin (SEQ ID NO:13).

FIGS. 3A–3C provide structures of representative modulating agents (SEQ ID NOS:6–9,11,14,16–18,24,26,31).

FIG. 4A shows the cells 24 hours after exposure to 100 μl water/1 ml culture medium (magnification 200×). FIGS. 4B and 4C show the cells 24 hours after exposure to 1 mg/mL N-Ac-IFVIDDKSG-NH$_2$ (SEQ ID NO:6) (magnifications of 200× and 100×, respectively). Arrows indicate rounded cells.

DETAILED DESCRIPTION OF THE INVENTION

Figure 3B:
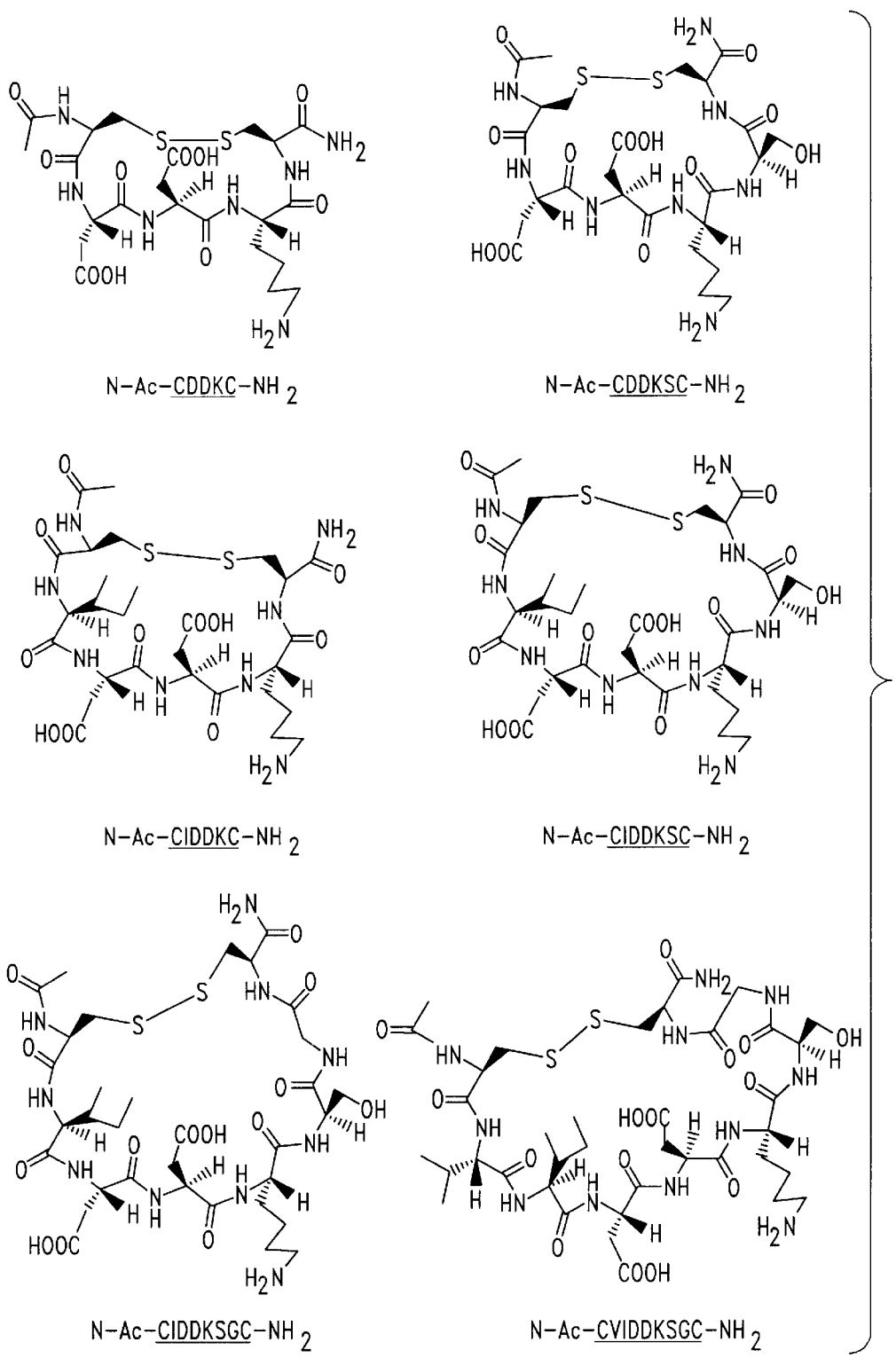

As noted above, the present invention provides methods for modulating cadherin-mediated processes, such as cell adhesion. The present invention is based upon the identification of a previously unknown cell adhesion recognition (CAR) sequence present in OB-cadherin. A modulating agent may comprise one or more OB-cadherin CAR sequences (or an analogue or peptidomimetic thereof), with or without one or more additional CAR sequences, as described below. Such peptide sequences may be present within a linear or cyclic peptide. Alternatively, or in addition, a modulating agent may comprise a polynucleotide encoding a peptide comprising one or more OB-cadherin CAR sequences and/or a substance (such as an antibody or antigen-binding fragment thereof) that specifically binds to an OB-cadherin CAR sequence.

In general, to modulate cadherin-mediated cell adhesion, a cell that expresses OB-cadherin is contacted with a cell adhesion modulating agent (also referred to herein as a "modulating agent") either in vivo or in vitro. Within certain aspects, the methods provided herein inhibit cell adhesion. Such methods may generally be used, for example, to treat diseases or other conditions characterized by undesirable cell adhesion or to facilitate drug delivery to a specific tissue or tumor. For example, such methods may be used to inhibit cell adhesion (e.g., cancer cell adhesion), as well as cancer invasion and metastasis. Alternatively, a modulating agent may, such as when linked to a matrix or to another modulating agent via a linker, be used to enhance cell adhesion. Such conjugates may be used, for example, to facilitate wound healing or the adhesion of implants.

CELL ADHESION MODULATING AGENTS

As noted above, the term "cell adhesion modulating agent," as used herein, refers to a molecule comprising at least one of the following:

(a) a native OB-cadherin CAR sequence;

(b) an analogue of a native OB-cadherin CAR sequence that is capable of modulating OB-cadherin-mediated cell adhesion;

(c) a non-peptide peptidomimetic of an OB-cadherin CAR sequence that is capable of modulating OB-cadherin-mediated cell adhesion;

(d) a substance, such as an antibody or antigen-binding fragment thereof, that specifically binds an OB-cadherin CAR sequence and/or (e) a polynucleotide encoding any of the foregoing peptide sequences.

A modulating agent may consist entirely of one or more of the above elements, or may additionally comprise further peptide and/or non-peptide regions. In general, peptide modulating agents and portions thereof may be linear or cyclic peptides.

A "native OB-cadherin CAR sequence" is an amino acid sequence that exists in a naturally occurring OB-cadherin and is capable of inhibiting OB-cadherin mediated cell adhesion, as described herein. Such sequences generally comprise at least three amino acid residues, preferably 4–15 amino acid residues, and more preferably 5–9 amino acid residues, and may be identified based on sequence homology to known OB-cadherin CAR sequences, which are provided herein, and based on the ability of a peptide comprising such a sequence to modulate OB-cadherin mediated cell adhesion within a representative assay as described herein.

A native OB-cadherin CAR sequence may be found within extracellular domain 1 of an OB-cadherin (FIG. 1B), such as a human or mouse OB-cadherin (sequences of extracellular domain 1 of human and mouse OB-cadherin are provided in FIG. 2 and SEQ ID NOs:12 and 13, respectively). Within certain embodiments, a native OB-cadherin CAR sequence comprises one or more of the following peptide sequences: DDK, IDDK (SEQ ID NO:32), DDKS (SEQ ID NO:33), VIDDK (SEQ ID NO:3), IDDKS (SEQ ID NO:4), VIDDKS (SEQ ID NO:34), DDKSG (SEQ ID NO:35), IDDKSG (SEQ ID NO:24), VIDDKSG (SEQ ID NO:36), FVIDDK (SEQ ID NO:37), FVIDDKS (SEQ ID NO:38), FVIDDKSG (SEQ ID NO:5), IFVIDDK (SEQ ID NO:39), IFVIDDKS (SEQ ID NO:40), or IFVIDDKSG (SEQ ID NO:6). In certain preferred embodiments, a modulating agent comprises a peptide (containing a native cadherin CAR sequence) in which at least one terminal amino acid residue is modified (e.g., the N-terminal amino group is modified by, for example, acetylation or alkoxybenzylation and/or an amide or ester is formed at the C-terminus). It has been found, within the context of the present invention, that the addition of at least one such group to a linear or cyclic peptide modulating agent improves the ability of the agent to modulate OB-cadherin mediated cell adhesion. For cyclic peptides, such terminal groups may be added to the N- and/or C-terminus of the linear peptide prior to cyclization. Certain preferred modulating agents contain modifications at the N- and C-terminal residues, such as N-Ac-IFVIDDKSG-NH$_2$ (SEQ ID NO:6). Other OB-cadherin CAR sequences provided herein are also preferably modified by the addition of such terminal groups.

The present invention further contemplates native OB-cadherin sequences from other organisms. Additional native OB-cadherin CAR sequences may be identified based upon sequence similarity to the human and mouse sequences provided herein, and the ability to modulate OB-cadherin mediated cell adhesion may be confirmed as described herein.

As noted above, modulating agents as described herein may comprise an analogue or peptidomimetic of an OB-cadherin CAR sequence. An analogue generally retains at least 50% of a native OB-cadherin CAR sequence, and modulates OB-cadherin-mediated cell adhesion as described herein. Such analogues may contain any of a variety of substitutions, additions, deletions and/or modifications (e.g., side chain modifications). Preferred substitutions are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity on polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of an OB-cadherin CAR sequence is the ability to modulate an OB-cadherin-mediated function, which may be evaluated using the representative assays provided herein.

A peptidomimetic is a non-peptidyl compound that is conformationally similar to a native OB-cadherin CAR sequence, such that it modulates an OB-cadherin-mediated function as described below. Such mimetics may be designed based on techniques that evaluate the three dimensional structure of the peptide. For example, Nuclear Magnetic Resonance spectroscopy (NMR) and computational techniques may be used to determine the conformation of an OB-cadherin CAR sequence. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate of the lowest energy conformation for the OB cadherin CAR sequence. This information can then be used to design peptidomimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation; ii) introduction of unsaturation which fixes the relative positions of the terminal and geminal substituents; and/or iii) cyclization, which fixes the relative positions of the sidechains. Peptidomimetics of OB-Cadherin CAR sequence may be synthesized where one or more of the amide linkages has been replaced by isosteres, substituents or groups which have the same size or volume such as —CH$_2$NH—, —CSNH—, —CH$_2$S—, —CH=CH—, —CH$_2$CH$_2$—, —CONMe— and others. These backbone amide linkages can be also be part of a ring structure (i.e., lactam). Peptidomimetics of OB-Cadherin CAR sequence may be designed where one or more of the side chain functionalities of the OB-cadherin CAR sequence can be replaced by groups that do not necessarily have the same size or volume, but have similar chemical and/or physical properties which produce similar biological responses. It should be understood that, within embodiments described below, an analogue or mimetic may be substituted for an OB-cadherin CAR sequence.

Without wishing to be bound by any particular theory, it is believed that the OB-cadherin CAR sequence is directly involved in the homophilic recognition between OB-cadherin molecules on adjacent cells. It is also believed that the CAR sequence, with or without immediate flanking sequences, is involved in a heterophilic interaction that may occur between OB-cadherin on the surface of lamellopodia of migratory cells and components of the extracellular matrix.

Modulating agents, or peptide portions thereof, may be linear or cyclic peptides. The term "cyclic peptide," as used herein, refers to a peptide or salt thereof that comprises (1) an intramolecular covalent bond between two non-adjacent residues and (2) at least one OB-cadherin CAR sequence or an analogue thereof. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. One or more of any of the above OB-cadherin CAR sequences, or an analogue or peptidomimetic thereof, may be incorporated into a cyclic peptide, with or without one or more other adhesion molecule binding sites, which may or may not be CARs. Additional adhesion molecule binding sites are described in greater detail below.

The size of a cyclic peptide ring generally ranges from 5 to about 15 residues, preferably from 5 to 10 residues. Additional residue(s) may be present on the N-terminal and/or C-terminal side of an OB-cadherin CAR sequence, and may be derived from sequences that flank a native OB-cadherin CAR sequence, with or without amino acid substitutions and/or other modifications. Flanking sequences for endogenous mouse and human OB-cadherin CAR sequences are shown in SEQ ID NOs:12 and 13. Alternatively, additional residues present on one or both sides of the CAR sequence(s) may be unrelated to an endogenous sequence (e.g., residues that facilitate cyclization, purification or other manipulation and/or residues having a targeting or other function). Within certain embodiments, a modulating agent may comprise a cyclic peptide comprising a sequence as recited above. Cyclic peptides specifically contemplated by the present invention include, but are not limited to, CDDKC (SEQ ID NO:7), CIDDKC (SEQ ID NO:41), CDDKSC (SEQ ID NO:42), CVIDDKC (SEQ ID NO:8), CIDDKSC (SEQ ID NO:9), CVIDDKSC (SEQ ID NO:43), CDDKSGC (SEQ ID NO:44), CIDDKSGC (SEQ ID NO:45), CVIDDKSGC (SEQ ID NO:31), CFVIDDKC (SEQ ID NO:46), CFVIDDKSC (SEQ ID NO:47), CFVIDDKSGC (SEQ ID NO:10), CIFVIDDKC (SEQ ID NO:48), CIFVIDDKSC (SEQ ID NO:49), or CIFVIDDKSGC (SEQ ID NO:11), DDDK(SEQ ID NO:50), DIDDK (SEQ ID NO:51), DVIDDK (SEQ ID NO:52), DFVIDDK (SEQ ID NO:53), DIFVIDDK (SEQ ID NO:54), EDDK(SEQ ID NO:55), EIDDK (SEQ ID NO:56), EVIDDK (SEQ ID NO:57), EFVIDDK (SEQ ID NO:58), EIFVIDDK (SEQ ID NO:59), KDDKD (SEQ ID NO:14), KIDDKD (SEQ ID NO:60), KDDKSD (SEQ ID NO:61), KVIDDKD(SEQ ID NO:62), KIDDKSD (SEQ ID NO:63), KVIDDKSD (SEQ ID NO:64), KDDKSGD (SEQ ID NO:65), KIDDKSGD (SEQ ID NO:26), KVIDDKSGD (SEQ ID NO:66), KFVIDDKD (SEQ ID NO:67), KFVIDDKSD (SEQ ID NO:68), KFVIDDKSGD (SEQ ID NO:69), KIFVIDDKD (SEQ ID NO:70), KIFVIDDKSD (SEQ ID NO:71), KIFVIDDKSGD (SEQ ID NO:72), VIDDK (SEQ ID NO:73), IDDKS (SEQ ID NO:74), VIDDKS (SEQ ID NO:75), DDKSG (SEQ ID NO:76), IDDKSG (SEQ ID NO:24) KDDKE (SEQ ID NO:77), KIDDKE (SEQ ID NO:78), KDDKSE (SEQ ID NO:79), KVIDDKE (SEQ ID NO:80), KIDDKSE (SEQ ID NO:81), KVIDDKSE (SEQ ID NO:82), KDDKSGE (SEQ ID NO:80), KIDDKSGE (SEQ ID NO:84), KVIDDKSGE (SEQ ID NO:85), KFVIDDKE (SEQ ID NO:86), KFVIDDKSE (SEQ ID NO:87), KFVIDDKSGE (SEQ ID NO:88), KIFVIDDKE (SEQ ID NO:89), KIFVIDDKSE (SEQ ID NO:90), or KIFVIDDKSGE (SEQ ID NO:91). Within the context of the present invention, underlined sequences are cyclized using any suitable method, as described herein.

Figure 3C:
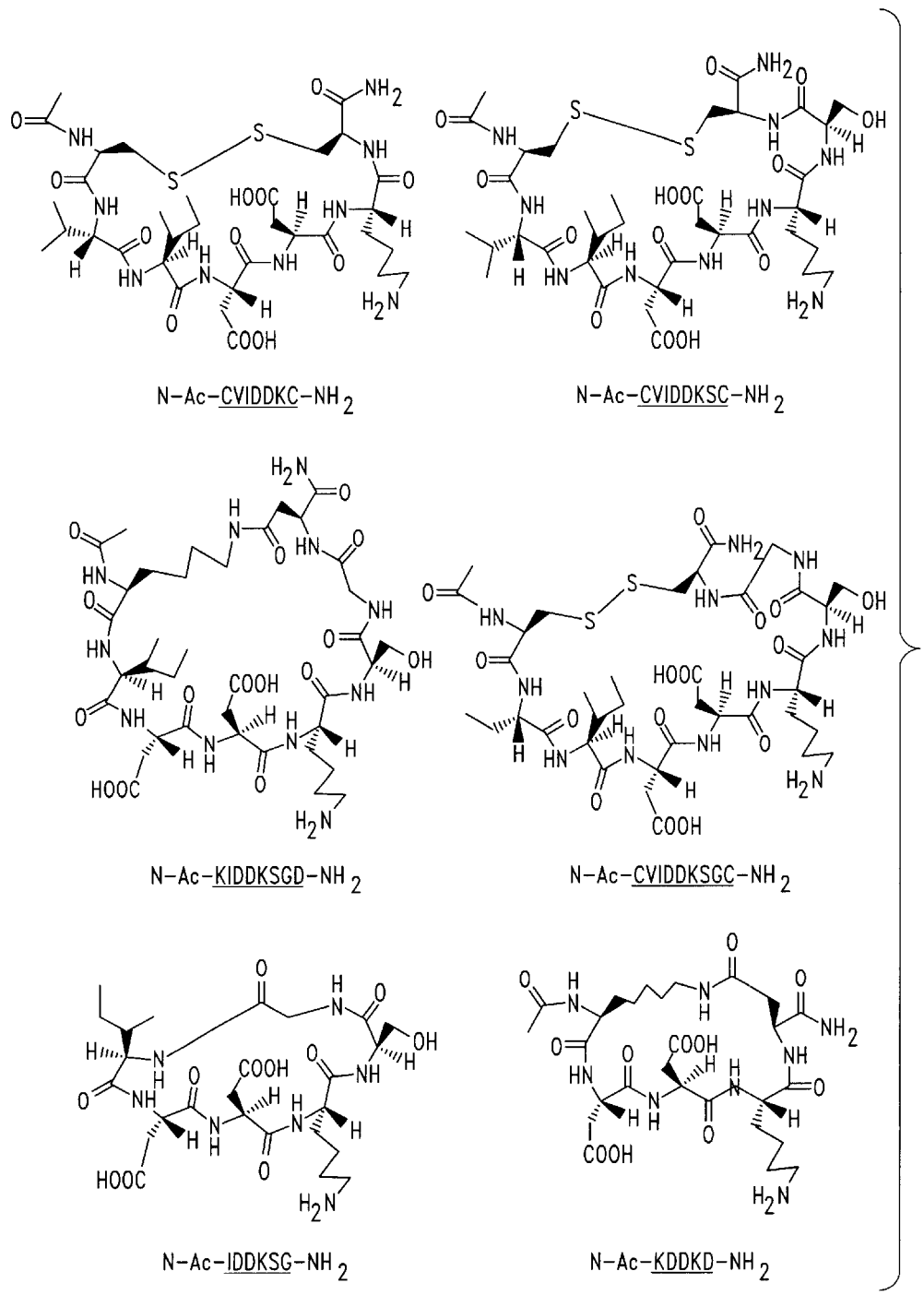

Within certain preferred embodiments, as discussed below, relatively small cyclic peptides that do not contain significant sequences flanking the CAR sequence are preferred for modulating OB-cadherin mediated cell adhesion. Such peptides may contain an N-acetyl group and a C-amide group (e.g., the 5-residue ring N-Ac-CDDKC-NH$_2$ (SEQ ID NO:7) or N-Ac-KDDKD-NH$_2$ (SEQ ID NO:14)). Small cyclic peptides may generally be used to specifically modulate cell adhesion of cancer and/or other cell types by topical administration or by systemic administration, with or without linking a targeting agent to the peptide, as discussed below. Certain representative cyclic peptides are shown in FIGS. 3A–3C.

Within embodiments in which inhibition of cell adhesion is desired, a modulating agent may contain one OB-cadherin CAR sequence, or multiple CAR sequences that are adjacent to one another (i.e., without intervening sequences) or in close proximity (i.e., separated by peptide and/or non-peptide linkers to give a distance between the OB-cadherin CAR sequences that ranges from about 0.1 to 400 nm). A linker may be any molecule (including peptide and/or non-peptide sequences) that does not contain a CAR sequence and that can be covalently linked to at least two peptide sequences. Using a linker, OB-cadherin CAR sequence-containing peptides and other peptide or protein sequences may be joined end-to-end (i.e., the linker may be covalently attached to the carboxyl or amino group of each peptide sequence), and/or via side chains. One linker that can be used for such purposes is (H$_2$N(CH$_2$)$_n$CO$_2$H), or derivatives thereof, where n ranges from 1 to 4. Other linkers that may be used will be apparent to those of ordinary skill in the art. Peptide and non-peptide linkers may generally be incorporated into a modulating agent using any appropriate method known in the art.

Within embodiments in which enhancement of cell adhesion is desired, a modulating agent may contain multiple OB-cadherin CAR sequences, or antibodies that specifically bind to such sequences, joined by linkers as described above. For enhancers of cadherin function, the linker distance should be 400–10,000 nm. One linker that can be used for such purposes is (H$_2$N(CH$_2$)$_n$CO$_2$H)$_m$, or derivatives thereof, where n ranges from 1 to 10 and m ranges from 1 to 4000. For example, if glycine (H$_2$NCH$_2$CO$_2$H) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Enhancement of cell adhesion may also be achieved by attachment of multiple modulating agents to a support material, as discussed further below.

A modulating agent as described herein may additionally comprise one or more CAR sequences for one or more different adhesion molecules (including, but not limited to, other CAMs) and/or one or more substances, such as antibodies or fragments thereof, that bind to such sequences. Linkers may, but need not, be used to separate such CAR sequence(s) and/or antibody sequence(s) from the CAR sequence(s) and/or each other. Such modulating agents may generally be used within methods in which it is desirable to simultaneously disrupt cell adhesion mediated by multiple adhesion molecules. As used herein, an "adhesion molecule" is any molecule that mediates cell adhesion via a receptor on a cell's surface. Adhesion molecules include cell adhesion proteins (e.g., other members of the cadherin gene superfamily, such as N-cadherin and E-cadherin; integrins; as well as extracellular matrix proteins such as laminin, fibronectin, collagens, vitronectin, entactin and tenascin. Preferred CAR sequences for inclusion within a modulating agent include the classical cadherin CAR sequence His-Ala-Val (HAV); Arg-Gly-Asp (RGD), which is bound by integrins (see Cardarelli et al., *J. Biol. Chem.* 267:23159–64, 1992); and/or Tyr-Ile-Gly-Ser-Arg (YIGSR; SEQ ID NO:15), which is bound by α6β1 integrin. Other such sequences that may be included, particularly for modulating agents intended to facilitate wound healing, are putative desmocollin (Dsc) and desmoglein (Dsg) CAR sequences (YAT, FAT, YAS and/or RAL). Using linkers, such modulating agents may form linear or branched structures. Within one embodiment, modulating agents having a branched structure comprise four different CAR sequences, such as IFVIDDKSG (SEQ ID NO:6), RGD, YIGSR (SEQ ID NO:15) and HAV. Bi-functional modulating agents that comprise the OB-cadherin CAR sequence joined via a linker to the classical cadherin CAR sequence are also preferred for certain embodiments. As noted above, linkers preferably produce a distance between CAR sequences ranging from 0.1 to 10,000 nm, more preferably ranging from 0.1–400 nm. A separation distance between recognition sites may generally be determined according to the desired function of the modulating agent.

The total number of CAR sequences (including the OB-cadherin CAR sequence, with or without other CAR sequences derived from one or more adhesion molecules) present within a modulating agent may range from 1 to a large number, such as 100, preferably from 1 to 10, and more preferably from 1 to 5. Peptide modulating agents comprising multiple CAR sequences typically contain from 6 (e.g., DDK-HAV) to about 1000 amino acid residues, preferably from 6 to 50 residues. When non-peptide linkers are employed, each CAR sequence of the modulating agent is present within a peptide that generally ranges in size from 3 to 50 residues in length, preferably from 4 to 25 residues, and more preferably from 5 to 15 residues.

As noted above, modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations, and the corresponding D-amino acids are designated by a lower case one letter symbol.

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and c-terminal amide groups are represented by —$NH_2$:

i) N-Ac-<u>Cys-Asp-Asp-Lys-Cys</u>-$NH_2$ (SEQ ID NO:7)

ii) N-Ac-<u>Cys-Ile-Asp-Asp-Lys-Ser-Gly-Cys</u>-$NH_2$ (SEQ ID NO:16)

iii) N-Ac-<u>Cys-Ile-Asp-Asp-Lys-Cys</u>-$NH_2$ (SEQ ID NO:17)

iv) N-Ac-<u>Cys-Asp-Asp-Lys-Ser-Cys</u>-$NH_2$ (SEQ ID NO:18)

v) N-Ac-<u>Cys-Ile-Asp-Asp-Lys-Ser-Cys</u>-$NH_2$ (SEQ ID NO:9)

vi) N-Ac-<u>Cys-Asp-Asp-Lys-Ser-Cys</u>-OH (SEQ ID NO:18)

vii) H-<u>Cys-Ile-Asp-Asp-Lys-Ser-Cys</u>-$NH_2$ (SEQ ID NO:9)

viii) N-Ac-<u>Cys-Asp-Asp-Lys-Pen</u>-$NH_2$ (SEQ ID NO:19)

ix) N-Ac-<u>Cys-Phe-Val-Ile-Asp-Asp-Lys-Ser-Gly-Cys</u>-$NH_2$ (SEQ ID NO:10)

x) N-Ac-<u>Cys-Ile-Phe-Val-Ile-Asp-Asp-Lys-Ser-Gly-Cys</u>-$NH_2$ (SEQ ID NO:11)

xi) N-Ac-Ile-<u>Tmc-Val-Ile-Asp-Asp-Lys-Ser-Cys</u>-Glu-$NH_2$ (SEQ ID NO:20)

xii) N-Ac-Ile-<u>Pmc-Val-Ile-Asp-Asp-Lys-Ser-Gly-Cys</u>-$NH_2$ (SEQ ID NO:21)

xiii) <u>Mpr-Val-Ile-Asp-Asp-Lys-Ser-Gly-Cys</u>-$NH_2$ (SEQ ID NO:22)

xiv) <u>Pmp-Val-Ile-Asp-Asp-Lys-Ser-Gly-Cys</u>-$NH_2$ (SEQ ID NO:23)

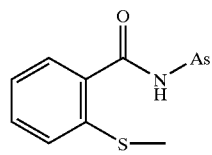

xv)

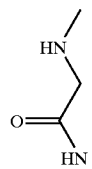

xvi)

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization). Two such cyclic peptides are <u>IDDKSG</u> (SEQ ID NO:24) with or without an N-terminal acetyl group and/or a C-terminal amide. Within another such embodiment, the linear peptide comprises a D-amino acid (e.g., <u>DDKsS</u>; SEQ ID NO:25). Alternatively, cyclization may be accomplished by linking one terminus and a residue side chain or using two side chains, as in <u>KDDKD</u> (SEQ ID NO:14) or <u>KIDDKSGD</u> (SEQ ID NO:26), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

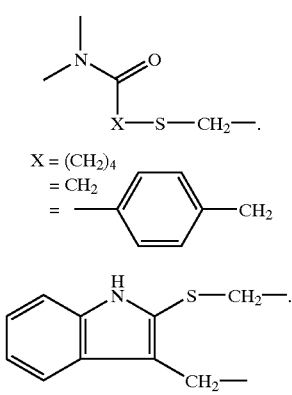

Cyclization may also be achieved using $\delta_1,\delta_1$-Ditryptophan (i.e., Ac-<u>Trp</u>-Gly-Gly-<u>Trp</u>-OMe) (SEQ ID NO:27), as shown below:

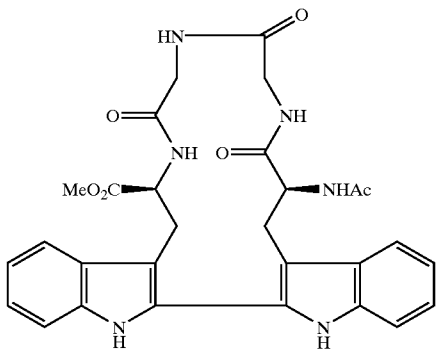

Representative structures of cyclic peptides are provided in FIGS. 3A–3C. The structures and formulas recited herein are provided solely for the purpose of illustration, and are not intended to limit the scope of the cyclic peptides described herein.

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous OB-cadherin or other adhesion molecule, or may encode a peptide comprising an OB-cadherin analogue or an antibody fragment that specifically binds to an OB cadherin CAR sequence. Such DNA sequences may be prepared based on known cDNA or genomic sequences, or from sequences isolated by screening an appropriate library with probes designed based on the sequences of known OB-cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous cadherin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, polynucleotides may also function as modulating agents. In general, such polynucleotides should be formulated to permit expression following administration to a mammal. Such formulations are particularly useful for therapeutic purposes, as described below. Those of ordinary skill in the art will appreciate that there are many ways to achieve expression of a polynucleotide within a mammal, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transfected cells) and/or a targeting moiety, such as a gene that encodes a ligand for a receptor on a specific target cell, to render the vector target specific. Targeting may also be accomplished using an antibody, by methods known to those of ordinary skill in the art. Other formulations for polynucleotides for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

As noted above, a modulating agent may additionally, or alternatively, comprise a substance such as an antibody or antigen-binding fragment thereof, that specifically binds to an OB-cadherin CAR sequence. As used herein, a substance is said to "specifically bind" to an OB-cadherin CAR sequence (with or without flanking amino acids) if it reacts at a detectable level with a peptide containing that sequence, and does not react detectably with peptides containing a different CAR sequence or a sequence in which the order of amino acid residues in the cadherin CAR sequence and/or flanking sequence is altered. Such antibody binding properties may generally be assessed using an ELISA, which may be readily performed by those of ordinary skill in the art and is described, for example, by Newton et al., *Develop. Dynamics* 197:1–13, 1993.

Polyclonal and monoclonal antibodies may be raised against an OB-cadherin CAR sequence using conventional techniques. See, e.g., Harlow and Lane, *Antibodies: A Laboratory Manual*, Cold Spring Harbor Laboratory, 1988. In one such technique, an immunogen comprising the CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for an OB-cadherin sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation and extraction. Antibodies having the desired activity may generally be identified using immunofluorescence analyses of tissue sections, cell or other samples where the target cadherin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

EVALUATION OF MODULATING AGENT ACTIVITY

Modulating agents as described above are capable of modulating OB-cadherin-mediated processes. The ability of the CAR sequence to bind to OB-cadherin may generally be evaluated using any binding assay known to those of ordinary skill in the art. For example, a Pharmacia Biosensor machine may be used, as discussed in Jonsson et al., *Biotechniques* 11:520–27, 1991. A specific example of a technology that measures the interaction of peptides with molecules can be found in Williams et al., *J. Biol. Chem.* 272, 22349–22354, 1997. Real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 μg/ml) in 10 mM Sodium Acetate, pH 4.0, according to the manufacturer's protocol. Approximately 2100–2600 resonance units (RU) of ligand may be immobilized, corresponding to a concentration of about 2.1–2.6 ng/mm$^2$. The chips may then coated be with OB-cadherin derivatized to biotin. Any non-specifically bound protein is removed.

To determine binding, test analytes (e.g., peptides containing the OB-cadherin CAR sequence) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds to OB-cadherin at a detectable level within such as assay. The level of binding is preferably at least that observed for a native OB-cadherin CAR-sequence under similar conditions.

The ability to modulate OB-cadherin-mediated function may be evaluated using any of a variety of in vitro assays designed to measure the effect of the peptide on a typical OB-cadherin response. As noted above, modulating agents may be capable of enhancing or inhibiting a OB-cadherin-mediated function. The ability of an agent to modulate cell adhesion may generally be evaluated in vitro by assaying the effect on adhesion between cancer cells. In general, a modulating agent is an inhibitor of cell adhesion if contact of the test cells with the modulating agent results in a discernible disruption of cell adhesion. Modulating agents that enhance cell adhesion (e.g., agents comprising multiple OB-cadherin CAR sequences and/or OB-cadherin CAR sequences linked to a support material) are considered to be modulators of cell adhesion if they are capable of promoting cell adhesion, as judged by plating assays to assess cancer cell adhesion to a modulating agent attached to a support material, such as tissue culture plastic.

Within certain cell adhesion assays, the addition of a modulating agent to cells that express OB-cadherin results in disruption of cell adhesion. An "OB-cadherin-expressing cell," as used herein, may be any type of cell that expresses OB-cadherin at a detectable level, using standard techniques such as immunocytochemical protocols (e.g., Blaschuk and Farookhi, *Dev. Biol.* 136:564–567, 1989). OB-cadherin-expressing cells include stromal, osteoblast and/or cancer cells. For example, such cells may be plated under standard conditions that, in the absence of modulating agent, permit cell adhesion. In the presence of modulating agent (e.g., 1 mg/mL), disruption of cell adhesion may be determined visually within 24 hours, by observing retraction of the cells from one another and the substratum.

For use within one such assay, the effect of a modulating agent on MDA-231 human breast cancer cells may be evaluated. According to a representative procedure, the cells may be plated at 10–20,000 cells per 35 mm tissue culture flasks containing DMEM with 5% FCS and sub-cultured periodically (Sommers et al., *Cell Growth Diffn* 2:365–72, 1991). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 2% paraformaldehyde for 30 minutes and then washed three times with PBS. Coverslips can be mounted and viewed by phase contrast microscopy.

In the absence of modulating agent, MDA-231 cells display an epithelial-like morphology and are well attached to the substratum. MDA-231 cells that are treated with a modulating agent that disrupts OB-cadherin mediated cell adhesion may assume a round shape and become loosely attached to the substratum within 48 hours of treatment with 1 mg/mL of modulating agent.

MODULATING AGENT MODIFICATION AND FORMULATIONS

A modulating agent as described herein may, but need not, be linked to one or more additional molecules. In particular, as discussed below, it may be beneficial for certain applications to link multiple modulating agents (which may, but need not, be identical) to a support material, such as a single molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an HAV or RGD sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, –Fab', Fab and F[v] fragments, which may be produced by conventional methods or by genetic or protein engineering. Linkage is generally covalent and may be achieved by, for example, direct condensation or other reactions, or by way of bi- or multi-functional linkers.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a pharmaceutical composition may further comprise a modulator of cell adhesion that is mediated by one or more molecules other than OB-cadherin. Such modulators may generally be prepared as described above, incorporating one or more non-OB-cadherin CAR sequences and/or antibodies thereto in place of the OB-cadherin sequence and antibodies. Such compositions are particularly useful for situations in which it is desirable to inhibit cell adhesion mediated by multiple cell adhesion molecules, such as other members of the cadherin gene superfamily such as the classical cadherins (e.g., N-cadherin and E-cadherin); integrins, as well as extracellular matrix proteins such as laminin, fibronectin, collagens, vitronectin, entactin and tenascin.

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antipsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 $\mu$g to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

MODULATING AGENT METHODS OF USE

In general, the modulating agents and compositions described herein may be used for modulating the adhesion of OB-cadherin-expressing cells. Such modulation may be performed in vitro and/or in vivo, preferably in a mammal such as a human, provided that an OB-cadherin expressing cell is ultimately contacted with a modulating agent. As noted above, modulating agents for purposes that involve the disruption of OB-cadherin-mediated cell adhesion may comprise an OB-cadherin CAR sequence, multiple OB-cadherin CAR sequences in close proximity and/or a substance (such as an antibody or an antigen-binding fragment thereof) that recognizes an OB-cadherin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the OB-cadherin CAR sequence by linkers. As noted above, such linkers may or may not comprise one or more amino acids. For enhancing cell adhesion, a modulating agent may contain multiple OB-cadherin CAR sequences or antibodies (or fragments), preferably separated by linkers, and/or may be linked to a single molecule or to a support material as described above.

Certain methods involving the disruption of cell adhesion as described herein have an advantage over prior techniques in that they block tumor cell adhesion. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

Within one aspect, methods are provided in which cell adhesion is diminished. In one such aspect, the present invention provides methods for reducing unwanted cellular adhesion by administering a modulating agent as described herein. Unwanted cellular adhesion can occur between tumor cells, between tumor cells and normal cells or between normal cells as a result of surgery, injury, chemotherapy, disease, inflammation or other condition jeopardizing cell viability or function. Preferred modulating agents for use within such methods comprise one or more of the sequences: DDK, IDDK (SEQ ID NO:32), DDKS (SEQ ID NO:33), VIDDK (SEQ ID NO:3), IDDKS (SEQ ID NO:4), VIDDKS (SEQ ID NO:34), DDKSG (SEQ ID NO:35), IDDKSG (SEQ ID NO:24), VIDDKSG (SEQ ID NO:36), FVIDDK (SEQ ID NO:37), FVIDDKS (SEQ ID NO:38), FVIDDKSG (SEQ ID NO:5), IFVIDDK (SEQ ID NO:39), IFVIDDKS (SEQ ID NO:40), or IFVIDDKSG (SEQ ID NO:6).

In one particularly preferred embodiment, a modulating agent is further capable of disrupting cell adhesion mediated by multiple adhesion molecules. Such an agent may comprise, in addition to an OB-cadherin CAR sequence, CAR sequences such as the classical cadherin CAR sequence HAV sequence, an RGD sequence, which is bound by integrins, and/or the occludin CAR sequence LYHY (SEQ ID NO:28), preferably separated from the OB-cadherin CAR sequence via a linker. Alternatively, separate modulators of cell adhesion mediated by other adhesion molecules may be administered in conjunction with the modulating agent(s), either within the same pharmaceutical composition or separately.

Topical administration of the modulating agent(s) is generally preferred, but other means may also be employed. Preferably, a fluid composition for topical administration (comprising, for example, physiological saline) comprises an amount of modulating agent as described above, and more preferably from 10 µg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within a further aspect, methods are provided for enhancing delivery of a drug to a tumor in a mammal, comprising administering a modulating agent in combination with a drug to a tumor-bearing mammal. Modulating agents for use within such methods include those designed to disrupt OB-cadherin, E-cadherin and/or N-cadherin mediated cell adhesion. For example, such a modulating agent may comprise an OB-cadherin CAR sequence, such as DDK, IDDK (SEQ ID NO:32), DDKS (SEQ ID NO:33), VIDDK (SEQ ID NO:3), IDDKS (SEQ ID NO:4), VIDDKS (SEQ ID NO:34), DDKSG (SEQ ID NO:35), IDDKSG (SEQ ID NO:24), VIDDKSG (SEQ ID NO:36), FVIDDK (SEQ ID NO:37), FVIDDKS (SEQ ID NO:38), FVIDDKSG (SEQ ID NO:5), IFVIDDK (SEQ ID NO:39), IFVIDDKS (SEQ ID NO:40), or IFVIDDKSG (SEQ ID NO:6) in combination with an E- and/or N-cadherin CAR sequence (e.g., HAV, SHAVSS (SEQ ID NO:29), AHAVDI (SEQ ID NO:30) or a derivative of such a sequence). Bi-functional modulating agents that comprise the classical cadherin CAR sequence with either flanking E-cadherin-specific sequences or flanking N-cadherin-specific sequences joined via a linker to the OB-cadherin CAR sequence are also preferred. Preferably, the peptide portion(s) of a modulating agent comprises 6–16 amino acids, since longer peptides are difficult to dissolve in aqueous solution and are more likely to be degraded by peptidases.

In one particularly preferred embodiment, a modulating agent is capable of disrupting cell adhesion mediated by multiple adhesion molecules. For example, a single branched modulating agent (or multiple agents linked to a single molecule or support material) may disrupt OB-cadherin, E-cadherin, N-cadherin, and integrin mediated cell adhesion. Such agents serve as multifunctional disrupters of cell adhesion. Alternatively, a separate modulator may be administered in conjunction with the modulating agent(s), either within the same pharmaceutical composition or separately. Preferred antibody modulating agents include Fab fragments directed against either the OB-cadherin or classical cadherin CAR sequences. The Fab fragments may be either incorporated into a modulating agent or within a separate modulator that is administered concurrently.

Preferably, the modulating agent and the drug are formulated within the same composition or drug delivery device prior to administration. In general, a modulating agent may enhance drug delivery to any tumor (e.g., breast tumor, stomach tumor or kidney tumor), and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., breast tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., taxol for breast cancer). In general, the amount of modulating agent administered varies with the method of administration and the nature of the tumor, within the typical ranges provided above, preferably ranging from about 1 µg/mL to about 2 mg/mL, and more preferably from about 10 µg/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting metastasis in a mammal. Preferred modulating agents for use within such methods include those that disrupt OB-cadherin, N-cadherin, E-cadherin and/or integrin mediated cell adhesion. For example, in addition to an OB-cadherin CAR sequence as provided above, a modulating agent may comprise a sequence such as HAV, SHAVSS (SEQ ID NO:29), AHAVDI (SEQ ID NO:30), RGD, YIGSR (SEQ ID NO:15)

or a derivative of such a sequence. Preferably, the peptide portion(s) of such modulating agents comprise 6–16 amino acids. Preferred antibody modulating agents include Fab fragments directed against either the OB-cadherin or classical cadherin CAR sequences. The Fab fragments may be either incorporated into a modulating agent or within a separate modulator that is administered concurrently.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. Preferably, the tumor is a breast tumor, stomach tumor or kidney tumor. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g., CEA or PSA).

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for inducing apoptosis in an OB-cadherin-expressing cell. In general, patients afflicted with cancer may benefit from such treatment. Certain preferred modulating agents for use within such methods comprise, in addition to an OB-cadherin CAR sequence, a sequence such as HAV, SHAVSS (SEQ ID NO:29), AHAVDI (SEQ ID NO:30), RGD, YIGSR (SEQ ID NO:15) or a derivative of such a sequence. Preferably, the peptide portion(s) of such modulating agents comprise 6–16 amino acids. Preferred antibody modulating agents include Fab fragments directed against either the OB-cadherin or classical cadherin CAR sequences. The Fab fragments may be either incorporated into a modulating agent or within a separate modulator that is administered concurrently. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

Within a related aspect, the present invention provides methods for treating obesity in a mammal, by using modulating agents that disrupt OB-cadherin function to inhibit adipocyte adhesion. Modulating agents as described herein may be administered alone, or in combination with other agents. The use of Fab fragments directed against OB-cadherin CAR sequence is also preferred. A modulating agent may be administered alone (e.g., via the skin) or within a pharmaceutical composition. Injection or topical administration as described above may be preferred. In other instances, the composition may be administered systemically.

In another embodiment, methods are provided for causing the regression of blood vessels for the treatment of conditions such as cancer, psoriasis, arthritis, and age-related macular degeneration. Cancer tumors are solid masses of cells, growing out of control, which require nourishment via blood vessels. The formation of new capillaries is a prerequisite for tumor growth and the emergence of metastases. Administration of the modulating agents described herein may disrupt blood vessels and cause them to regress, thereby providing effective therapy for patients afflicted with diseases such as cancer. Certain preferred modulating agents for use within such methods comprise, in addition to an OB-cadherin CAR sequence, a sequence such as HAV and RGD, or a derivative of such a sequence. Preferably, the peptide portion(s) of such modulating agents comprise 6–16 amino acids. Preferred antibody modulating agents include Fab fragments directed against the OB-cadherin CAR sequence, with or without Fab fragments directed against one or more classical cadherin CAR sequences. The Fab fragments may be either incorporated into a modulating agent or within a separate modulator that is administered concurrently. Administration may be topical, via injection or by other means, and the addition of a targeting agent may be beneficial, particularly when the administration is systemic. Suitable modes of administration and dosages depend upon the location and nature of the pericytes for which disruption of cell adhesion is desired but, in general, dosages may vary as described above. The effectiveness of the cancer treatment or inhibition of metastasis may be evaluated using well known clinical observations such as the level of serum markers (e.g., CEA or PSA). The addition of a targeting agent may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumor to maintain growth and microscopically by an absence of nerves at the periphery of the tumor.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient. Certain preferred modulating agents for use within such methods comprise, in addition to an OB-cadherin CAR sequence, a sequence such as LYHY (the occludin CAR sequence; SEQ ID NO:28) and HAV, or a derivative of such a sequence. Preferably, the peptide portion(s) of such modulating agents comprise 6–16 amino acids. Preferred antibody modulating agents include Fab fragments directed against either the OB-cadherin, classical cadherin, and occludin CAR sequences. The Fab fragments may be either incorporated into a modulating agent or within a separate modulator that is administered concurrently. In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

The present invention also provides methods for increasing vasopermeability in a mammal by administering one or more modulating agents or pharmaceutical compositions. Within blood vessels, endothelial cell adhesion (mediated by N-cadherin and occludin) results in decreased vascular permeability. Disruption of pericyte adhesion (mediated by OB-cadherin) destabilizes blood vessels and causes them to become more permeable. Accordingly, modulating agents as described herein that decrease OB-cadherin, N-cadherin and occludin mediated adhesion may be used to increase vascular permeability. Certain preferred modulating agents for use within such methods comprise, in addition to an OB-cadherin CAR sequence, a sequence such as LYHY (the occludin CAR sequence; SEQ ID NO:28) HAV and RGD, or a derivative of such a sequence. Preferably, the peptide portion(s) of such modulating agents comprise 6–16 amino acids. Preferred antibody modulating agents include Fab fragments directed against either the OB-cadherin, classical cadherin, and occludin CAR sequences. The Fab fragments may be either incorporated into a modulating agent or within a separate modulator that is administered concurrently.

In certain other aspects, the present invention provides methods for enhancing adhesion of OB-cadherin-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising either HAV or RGD sequences may be attached to the same matrix, preferably in an alternating pattern). Such matrices may be used in contexts in which it is desirable to enhance adhesion mediated by multiple cell adhesion molecules. Alternatively, the modulating agent itself may comprise multiple OB-cadherin CAR sequences or antibodies (or fragments thereof), separated by linkers as described above. Either way, the modulating agent(s) function as a "biological glue" to bind multiple OB-cadherin-expressing cells within a variety of contexts.

Within one such aspect, modulating agents comprising the OB-cadherin CAR sequence and/or multiple modulating agents linked to a single molecule or support material may be used to facilitate wound healing and/or reduce scar tissue in a mammal. Peptides that may be linked to a support, and/or to one another via a linker, to generate a suitable modulating agent include, but are not limited to, one or more OB cadherin CAR sequences, such as DDK, IDDK (SEQ ID NO:32), DDKS (SEQ ID NO:33), VIDDK (SEQ ID NO:3), IDDKS (SEQ ID NO:4), VIDDKS (SEQ ID NO:34), DDKSG (SEQ ID NO:35), IDDKSG (SEQ ID NO:24), VIDDKSG (SEQ ID NO:36), FVIDDK (SEQ ID NO:37), FVIDDKS (SEQ ID NO:38), FVIDDKSG (SEQ ID NO:5), IFVIDDK (SEQ ID NO:39), IFVIDDKS (SEQ ID NO:40), or IFVIDDKSG (SEQ ID NO:6), in combination with one or more of HAV, SHAVSS (SEQ ID NO:29), AHAVDI (SEQ ID NO:30), or a derivative of such a sequence. Preferred antibody modulating agents include Fab fragments directed against either the OB-cadherin or E-cadherin CAR sequences. Modulating agents that are linked to a biocompatible and biodegradable matrix such as cellulose or collagen are particularly preferred. For use within such methods, a modulating agent should have a free amino or hydroxyl group. The modulating agents are generally administered topically to the wound, where they may facilitate closure of the wound and may augment, or even replace, stitches. Similarly, administration of matrix-linked modulating agents may facilitate cell adhesion in skin grafting and prosthetic implants, and may prolong the duration and usefulness of collagen injection. In general, the amount of matrix-linked modulating agent administered to a wound, graft or implant site varies with the severity of the wound and/or the nature of the wound, graft, or implant, but may vary as discussed above. Multi-functional modulating agents comprising an OB-cadherin sequence, a classical cadherin CAR sequence (HAV), the CAR sequence bound by certain integrins (RGD), as well as putative desmocollin (Dsc) and desmoglein (Dsg) CAR sequences (YAT, FAT, YAS and/or RAL) may also be used as potent stimulators of wound healing and/or to reduce scar tissue. Alternatively, one or more separate modulators of classical cadherin-, integrin-, Dsc- and/or Dsg-mediated cell adhesion may be administered in conjunction with the modulating agent(s), either within the same pharmaceutical composition or separately.

Within another aspect, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Other aspects of the present invention provide methods that employ antibodies raised against the modulating agents for diagnostic and assay purposes. Assays typically involve using an antibody to detect the presence or absence of OB-cadherin (free or on the surface of a cell), or proteolytic fragment containing the EC1 domain in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual,* Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target cadherin, or a proteolytic fragment containing the EC1 domain and encompassing the CAR sequence, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody, and as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of OB-cadherin in a sample is a two-antibody sandwich assay. This assay may be performed by first contacting an antibody that has been immobilized on a solid support, commonly the well of a microtiter plate, with the biological sample, such that the OB-cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme, dye, radionuclide, luminescent group, fluorescent group or biotin) capable of binding to a different site on the cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, modulating agents or antibodies (or fragments thereof) may be used to facilitate cell identification and sorting in vitro or imaging in vivo, permitting the selection of cells expressing OB-cadherin (or different OB-cadherin levels). Preferably, the modulating agent(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating OB-cadherin-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate OB-cadherin-mediated cell adhesion.

The following examples are offered by way of illustration and not by way of limitation.

EXAMPLES

Example 1

Preparation of Representative Modulating Agents

This Example illustrates the solid phase synthesis of representative peptide modulating agents.

The peptides were synthesized on a 431A Applied Biosystems peptide synthesizer using p-Hydroxymethylphenoxymethyl polystyrene (HMP) resin and standard Fmoc chemistry. After synthesis and deprotection, the peptides were de-salted on a Sephadex G-10 column and lyophilized. The peptides were analyzed for purity by analytical HPLC, and in each case a single peak was observed. Peptides were made as stock solutions at 10 to 25 mg/mL in dimethylsulfoxide (DMSO) or water and stored at −20° C. before use.

Example 2

Disruption of Human Breast Cancer Cell Adhesion

Figure 4A:
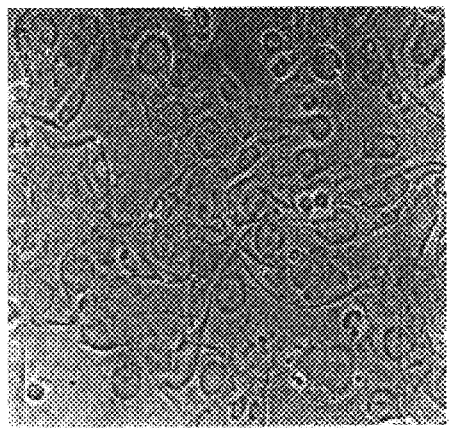
FIGS. 4A–4C are photographs showing cultures of human breast cancer cells in the presence (FIGS. 4B and 4C) and absence (FIG. 4A) of a representative linear peptide.
Figure 4B:
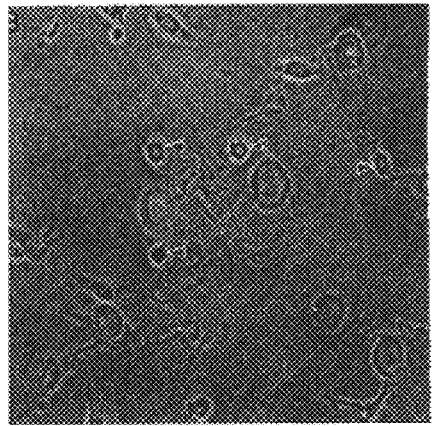
Figure 4C:
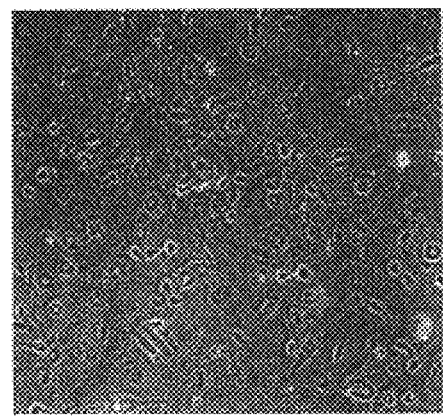

This Example illustrates the ability of a representative linear peptide to disrupt human breast epithelial cell adhesion. MDA-MB-231 human breast cancer cells (Lombardi Cancer Research Center, Washington, DC) were used in these experiments. They express cadherin-11 (also known as OB-cadherin) but not N-cadherin or E-cadherin. The cells were plated (~50,000 cells) on glass coverslips and cultured for 24 hours in DMEM medium containing 5% serum. Peptides (N-Ac-IFVIDDKSG-NH$_2$ (SEQ ID NO:6) and H-IFVIDDKSG-OH (SEQ ID NO:6)) were dissolved in sterile water (10 mg/ml), and 100 µl of each peptide stock solution was added to 1 ml of DMEM medium containing 5% serum. Control cells had 100 µl of water added to the medium. Cells were monitored by phase contrast microscopy. After 24 hours cells were fixed in formaldehyde. After 24 hours, neither the peptide H-IFVIDDKSG-OH (SEQ ID NO:6) nor water had an effect on cell morphology (FIG. 4A). The cells treated with either water or H-IFVIDDKSG-OH (SEQ ID NO:6) remained flattened and well-attached to the substratum. In contrast, the cells treated with N-Ac-IFVIDDKSG-NH$_2$ (SEQ ID NO:6) rounded up from each other and were not well-attached to the substratum (FIGS. 4A and 4B; arrows indicate rounded cells). These results demonstrate that the peptide N-Ac-IFVIDDKSG-NH$_2$ (SEQ ID NO:6) interferes with cell adhesion. The amino acid sequence of this peptide is identical to that which is found in the first extracellular domain of OB-cadherin.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A cell adhesion modulating agent, wherein the agent is a peptide four to nine amino acids in length that, at a concentration of 1 mg/mL, detectably inhibits OB-cadherin mediated cell adhesion, and wherein the peptide consists of (a) a native OB-cadherin CAR that comprises the sequence DDK and (b) optionally, a residue on one or both sides of the CAR sequence to facilitate cyclization.

2. A modulating agent according to claim 1, comprising one or more peptide sequences selected from the group consisting of DDK, IDDK (SEQ ID NO:32), DDKS (SEQ ID NO:33), VIDDK (SEQ ID NO:3), IDDKS (SEQ ID NO:4), VIDDKS (SEQ ID NO:34), DDKSG (SEQ ID NO:35), IDDKSG (SEQ ID NO:24), VIDDKSG (SEQ ID NO:36), FVIDDK (SEQ ID NO:37), FVIDDKS (SEQ ID NO:38), FVIDDKSG (SEQ ID NO:5), IFVIDDK (SEQ ID NO:39), IFVIDDKS (SEQ ID NO:40), and IFVIDDKSG (SEQ ID NO:6).

3. A modulating agent according to claim 1, wherein the peptide is a cyclic peptide.

4. A modulating agent according to claim 1 linked to a support material.

5. A modulating agent according to claim 4, wherein the support material is a polymeric matrix.

6. A modulating agent according to claim 4, wherein the solid support is selected from the group consisting of plastic dishes, plastic tubes, sutures, membranes, ultra thin films, bioreactors and microparticles.

7. A cell adhesion modulating agent linked to a drug, wherein the agent is a 3–50 amino acid peptide that, at a concentration of 1 mg/mL, detectably inhibits OB-cadherin mediated cell adhesion, and wherein the peptide consists of (a) a native OB-cadherin CAR sequence that comprises the sequence DDK and (b) optionally, a residue on one or both sides of the CAR sequence to facilitate cyclization.

8. A cell adhesion modulating agent linked to a detectable marker, wherein the agent is a 3–50 amino acid peptide that, at a concentration of 1 mg/mL, detectably inhibits OB-cadherin mediated cell adhesion, and wherein the peptide consists of (a) a native OB-cadherin CAR sequence that comprises the sequence DDK and (b) optionally a residue on one or both sides of the CAR sequence to facilitate cyclization.

9. A cell adhesion modulating agent linked to a targeting agent, wherein the modulating agent is a 3–50 amino acid peptide that, at a concentration of 1 mg/mL, detectably inhibits OB-cadherin mediated dell adhesion, and wherein the peptide consists of (a) a native OB-cadherin CAR sequence that comprises the sequence DDK and (b) optionally, a residue on one or both sides of the CAR sequence to facilitate cyclization.

10. A cell adhesion modulating agent that is a 3–50 amino acid peptide that, at a concentration of 1 mg/mL, detectably inhibits OB-cadherin mediated cell adhesion, wherein the peptide consists of (i) a native OB-cadherin CAR sequence that comprises the sequence DDK and (ii) optionally, a residue on one or both sides of the CAR sequence to facilitate cyclization, wherein the agent further comprises one or more of:

(a) a cell adhesion recognition sequence selected from the group consisting of HAV, RGD, YIGSR (SEQ ID NO:15), YAT, FAT, YAS, RAL, LYHY, SHAVSS (SEQ ID NO:29) and AHAVDI (SEQ ID NO:30); and/or (b) an antibody or antigen-binding fragment thereof that specifically binds to a CAR sequence selected from the group consisting of HAV, RGD, YIGSR (SEQ ID NO:15), YAT, FAT, YAS, RAL, LYHY, SHAVSS (SEQ ID NO:29) and AHAVDI (SEQ ID NO:30).

11. A composition comprising:

(a) a cell adhesion modulating agent that is a 3–50 amino acid peptide that, at a concentration of 1 mg/mL, detectably inhibits OB-cadherin mediated cell adhesion, wherein the peptide consists of (i) a native OB-cadherin CAR sequence that comprises the sequence DDK and (ii) optionally, a residue on one or both sides of the CAR sequence to facilitate cyclization, in combination with (b) a pharmaceutically acceptable carrier.

12. A composition according to claim 11, further comprising a drug.

13. A composition according to claim 11, wherein the cell adhesion modulating agent is present within a sustained-release formulation.

14. A composition according to claim 13, further comprising one or more of:

(a) a peptide comprising a cell adhesion recognition sequence selected from the group consisting of HAV, RGD, YIGSR (SEQ ID NO:15), YAT, FAT, YAS, RAL, LYHY, SHAVSS (SEQ ID NO:29) and AHAVDI (SEQ ID NO:30); and/or (b) an antibody or antigen-binding fragment thereof that specifically binds to a CAR sequence selected from the group consisting of HAV, RGD, YIGSR (SEQ ID NO:15), YAT, FAT, YAS, RAL, LYHY, SHAVSS (SEQ ID NO:29) and AHAVDI (SEQ ID NO:30).

* * * * *

UNITED STATES PATENT AND TRADEMARK OFFICE
CERTIFICATE OF CORRECTION

PATENT NO.    : 6,472,367 B1
DATED         : October 29, 2002
INVENTOR(S)   : Orest W. Blaschuk et al.

It is certified that error appears in the above-identified patent and that said Letters Patent is hereby corrected as shown below:

<u>Title page,</u>
Item [54], the title should read as -- PEPTIDE AGENTS FOR MODULATING OB-CADHERIN MEDIATED CELL ADHESION --.

Signed and Sealed this

Tenth Day of June, 2003

JAMES E. ROGAN
*Director of the United States Patent and Trademark Office*